United States Patent
Kojiri et al.

[11] Patent Number: 5,804,564
[45] Date of Patent: Sep. 8, 1998

[54] ANTITUMOR INDOLOPYRROLOCARBAZOLE DERIVATIVES

[75] Inventors: Katsuhisa Kojiri; Hisao Kondo; Hiroharu Arakawa; Mitsuru Ohkubo; Hiroyuki Suda, all of Tsukuba, Japan

[73] Assignee: Banyu Pharmaceutical Co., Ltd., Tokyo, Japan

[21] Appl. No.: 737,382

[22] PCT Filed: May 2, 1995

[86] PCT No.: PCT/JP95/00868

§ 371 Date: Nov. 8, 1996

§ 102(e) Date: Nov. 8, 1996

[87] PCT Pub. No.: WO95/30682

PCT Pub. Date: Nov. 16, 1995

Related U.S. Application Data

[63] Continuation-in-part of Ser. No. 255,980, Jun. 8, 1994, Pat. No. 5,591,842.

[30] Foreign Application Priority Data

May 9, 1994 [JP] Japan ..................................... 6-119483
Jun. 3, 1994 [JP] Japan ..................................... 6-145648

[51] Int. Cl.⁶ ............................ A61K 31/70; C07H 17/02
[52] U.S. Cl. ............................ 514/27; 514/43; 536/17.7; 536/18.7; 536/27.1; 536/29.1
[58] Field of Search ........................ 536/7.7, 18.7, 536/27.1, 29.1; 514/27, 43

[56] References Cited

U.S. PATENT DOCUMENTS

| | | | |
|---|---|---|---|
| 4,552,842 | 11/1985 | Nettleton et al. | 435/75 |
| 4,785,085 | 11/1988 | Kaneko et al. | 536/27.1 |
| 4,808,613 | 2/1989 | Kaneko et al. | 514/42 |
| 4,912,107 | 3/1990 | Kleinschroth et al. | 514/410 X |
| 4,923,986 | 5/1990 | Murakat et al. | 540/545 |
| 5,015,578 | 5/1991 | Schroeder et al. | 435/119 |
| 5,043,335 | 8/1991 | Kleinschroth et al. | 514/211 |
| 5,073,633 | 12/1991 | Schroeder et al. | 540/545 |
| 5,106,864 | 4/1992 | Suda et al. | 548/416 X |
| 5,158,938 | 10/1992 | Lam et al. | 514/42 |
| 5,227,396 | 7/1993 | Laakso et al. | 514/410 |
| 5,326,754 | 7/1994 | Lam et al. | 514/42 |
| 5,344,823 | 9/1994 | Lam et al. | 514/43 |
| 5,591,842 | 1/1997 | Kojiri et al. | 536/27.1 |

FOREIGN PATENT DOCUMENTS

| | | |
|---|---|---|
| 58351 | 1/1992 | Australia . |
| 0328000 | 12/1989 | European Pat. Off. ............... 548/416 |
| 0388956 | 11/1990 | European Pat. Off. . |
| 528 030 | 2/1993 | European Pat. Off. . |
| 3835842 | 1/1990 | Germany ............................... 548/416 |
| 91-20277 | 4/1991 | Japan . |
| 9118003 | 7/1991 | WIPO . |

OTHER PUBLICATIONS

Kaneko et al., Two Synthetic Approaches to Rebeccamycin, Tetrahedron Letters, vol. 26, No. 34, pp. 4015–4018, 1985.
Joyce, et al. J. Org. Chem. 52, No. 7 (1987) pp. 1177–1185.
Kaneko, et al. J. Antibiotics, vol. XLIII, No. 1 (1989) pp. 125–127.
47th Japan Society of Cancer General Meeting Article (1988) pp. 12–15.
Kojiri, et al. J. Antibiotics, vol. 44, No. 7 (7/91) pp. 723–728.
Hughes, et al. J. Chem. Soc. Perkin Trans. 1, (1990) pp. 2475–2480.
Reynolds, et al. J. Am. Chem. Soc. 60, (Oct. 1988) pp. 2559–2561.
Bush, et al. J. Antibiotics, vol. 40, (1987) pp. 668–678.

Primary Examiner—Mukund J. Shah
Assistant Examiner—Deepak R. Rao
Attorney, Agent, or Firm—Sherman & Shalloway

[57] ABSTRACT

This invention relates to compounds of the general formula

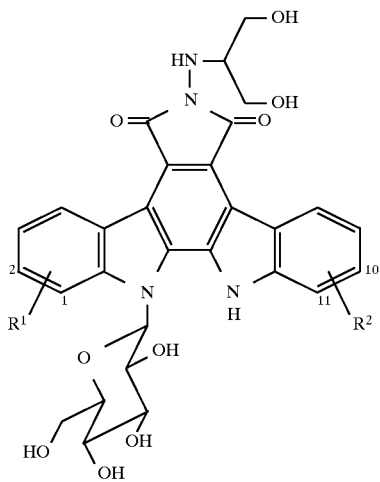

or pharmaceutically salts thereof, wherein $R^1$ and $R^2$ each represent an OH group, $R^1$ is located at the 1- or 2-position, $R^2$ is located at the 10- or 11-position, $R^2$ is located at the 11-position when $R^1$ is located at the 1-position, and $R^2$ is located at the 10-position when $R^1$ is located at the 2-position.

The compounds of the present invention have an excellent antitumor effect and are hence useful as antitumor agents in the field of medicine.

8 Claims, No Drawings

ANTITUMOR INDOLOPYRROLOCARBAZOLE DERIVATIVES

This is a national phase application of PCT/JP95/00868 filed May 2, 1995 and also a continuation-in-part of application Ser. No. 08/255,980, filed Jun. 8, 1994 which is now U.S. Pat. No. 5,591,842.

TECHNICAL FIELD

This invention relates to novel indolopyrrolocarbazole derivatives which are useful in the field of medicine and, more specifically, inhibit the growth of tumor cells and thereby exhibit an antitumor effect, their intermediates, processes for preparing them, and their use.

BACKGROUND ART

In the field of cancer chemotherapy, a large number of compounds have already been put to practical use as antitumor agents. However, their activities against various types of tumors are not necessarily satisfactory, and the problem of tolerance of tumor cells to these antitumor agents complicates their use for clinical purposes [see the Proceedings of the 47th General Meeting of the Japan Cancer Society, pp. 12–15 (1988)].

Under these circumstances, the development of novel cancerocidal substances are invariably desired in the field of cancer therapy. Among others, there is a need for substances which overcome the problem of tolerance to the existing cancerocidal substances and exhibit effectiveness against such types of cancers as cannot be effectively controlled by the existing cancerocidal substances.

In view of the above-described state of the art, the present inventors screened a wide variety of microbial metabolites, found a novel compound BE-13793C having antitumor activity (12,13-dihydro-1,11-dihydroxy-5H-indolo[2,3-a]pyrrolo[3,4-c]carbazole-5,7(6H)-dione), and disclosed it [see Japanese Laid-Open Patent No. 20277/'91 and the Journal of Antibiotics, Vol. 44, pp. 723–728 (1991)].

Thereafter, they created an indolopyrrolocarbazole compound having excellent antitumor activity by a chemical modification of BE-13793C, and disclosed it (see International Publication No. WO91/18003 and European Patent Laid-Open No. EP0545195 A1).

A problem to be solved by the present invention is to create a compound having more excellent antitumor activity than the indolopyrrolocarbazole-derived antitumor substances disclosed in the prior patent application (International Publication No. WO91/18003 and European Patent Laid-Open No. EP0545195 A1).

DISCLOSURE OF THE INVENTION

The present inventors have synthesized a large number of indolopyrrolocarbazole derivatives and have examined their antitumor activities, with a view to creating a compound having more excellent antitumor activity than the indolopyrrolocarbazole-derived antitumor compounds which were previously disclosed. As a result, it has now been found that the compounds represented by the following general formula [I] are novel compounds having very excellent antitumor activity, stability and safety.

Thus, the present invention relates to the compounds of the general formula

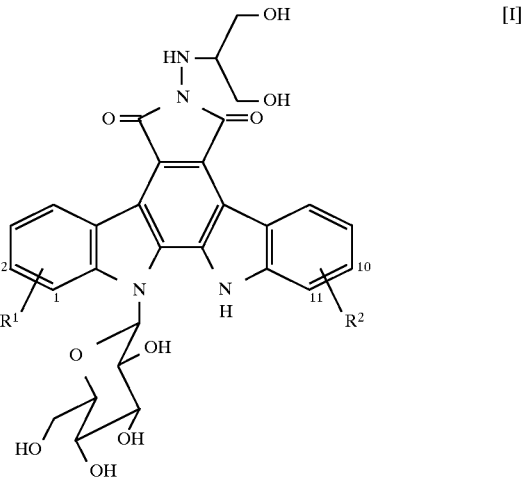

[I]

wherein $R^1$ and $R^2$ each represent an OH group, $R^1$ is located at the 1- or 2-position, $R^2$ is located at the 10- or 11-position, $R^2$ is located at the 11-position when $R^1$ is located at the 1-position, and $R^2$ is located at the 10-position when $R^1$ is located at the 2-position, or pharmaceutically acceptable salts thereof, their intermediates, processes for preparing them, and their use.

The compounds of the present invention and their intermediates can be prepared according to the processes represented by the following procedures A to E.

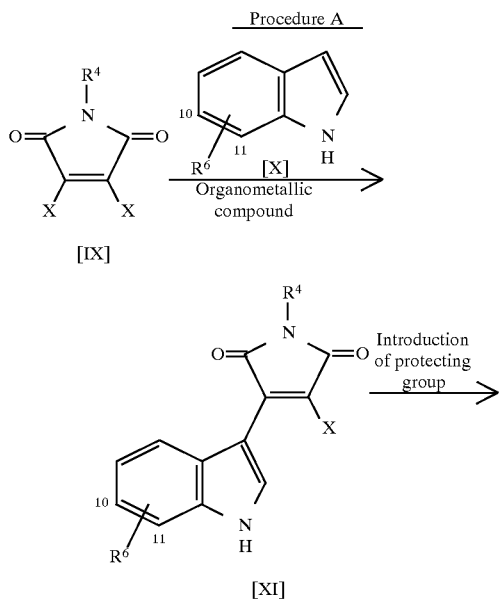

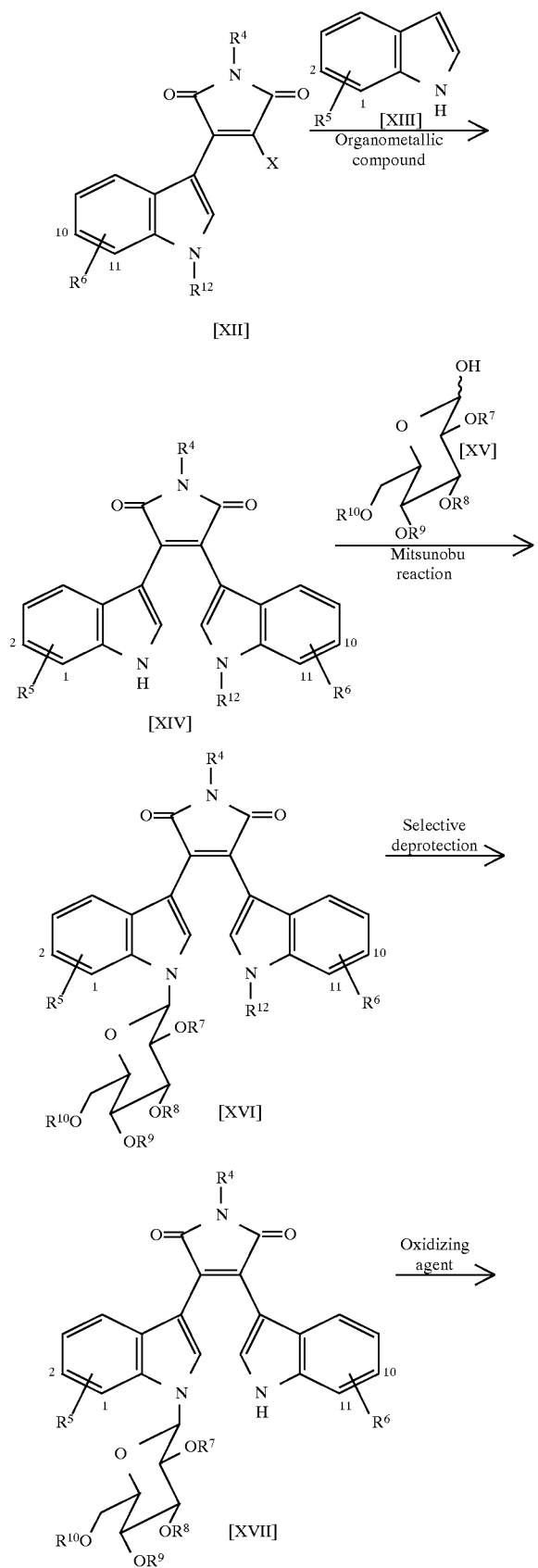
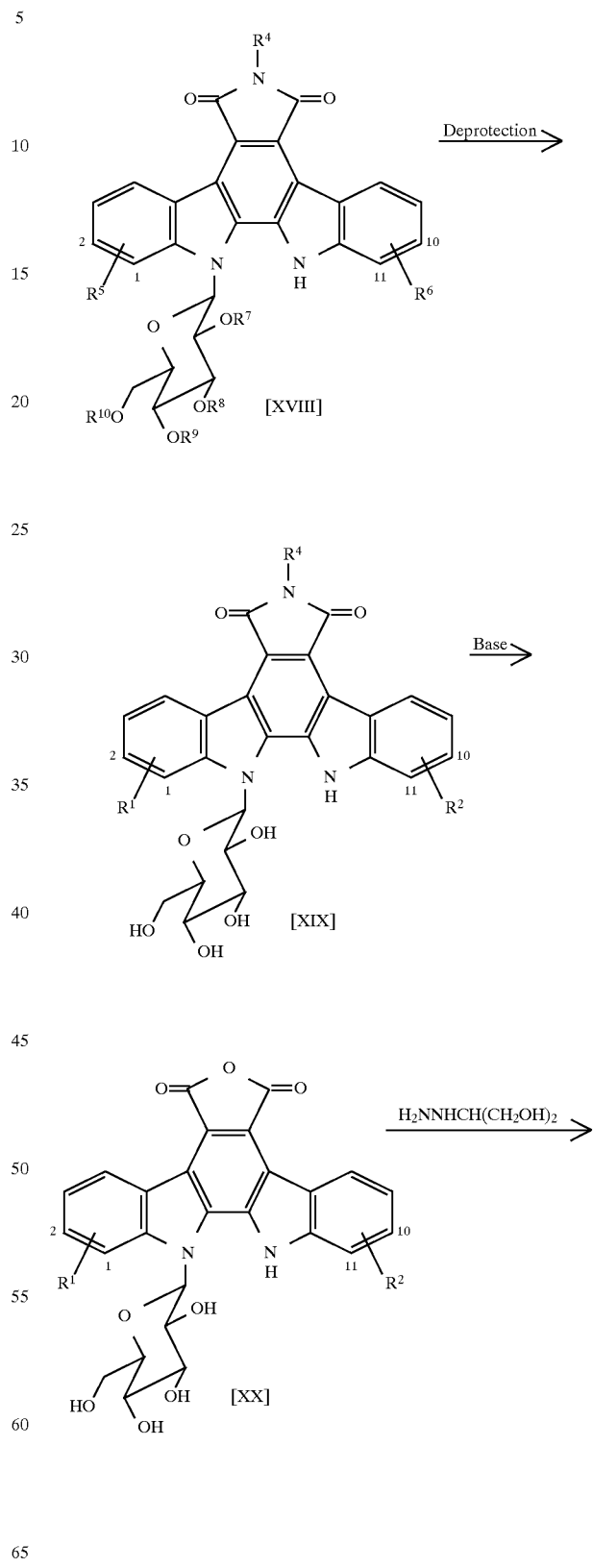

5,804,564
5
-continued
Procedure A
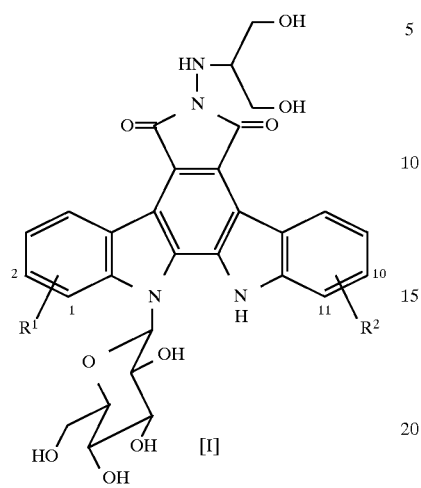
[I]
Procedure B
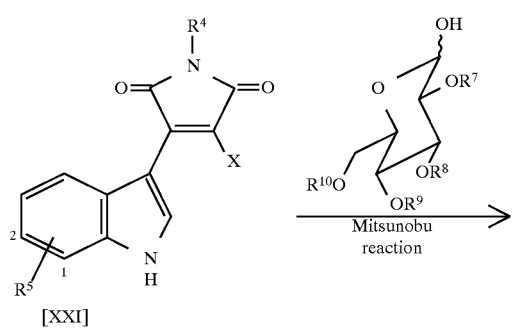
[XXI]
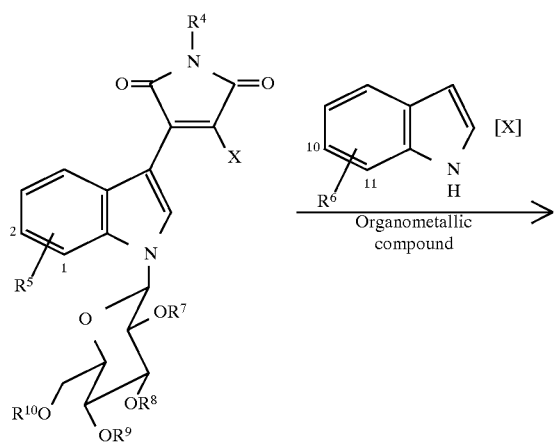
[V]
6
-continued
Procedure B
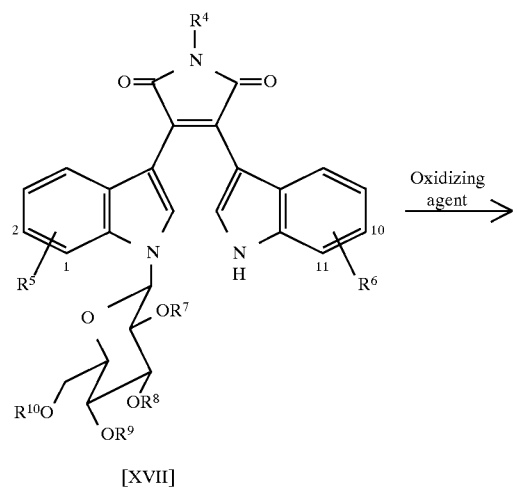
[XVII]
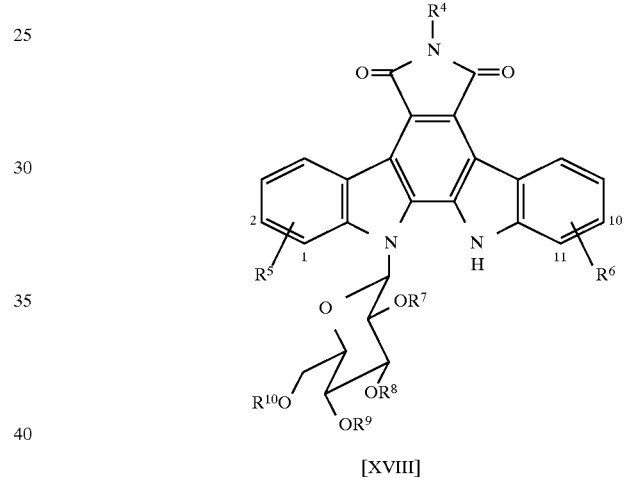
[XVIII]
Procedure C
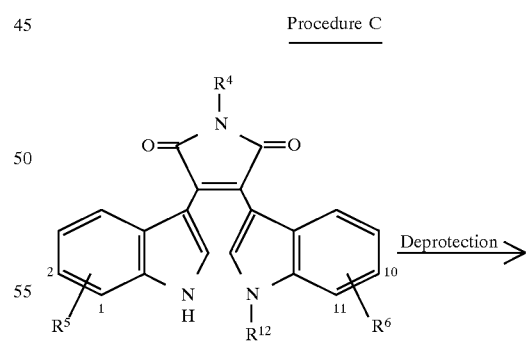
[XIV]

-continued
Procedure C
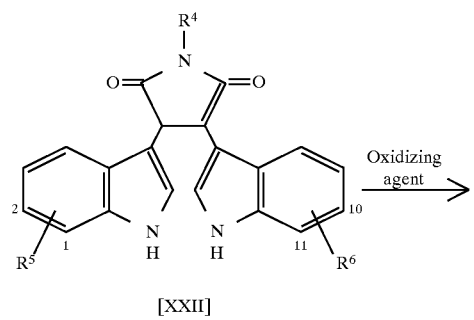
[XXII]
Oxidizing agent →
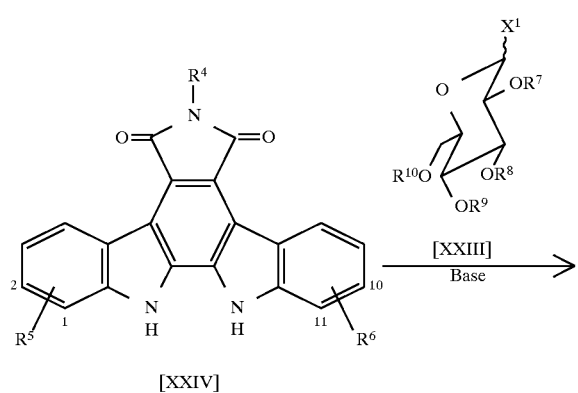
[XXIV]
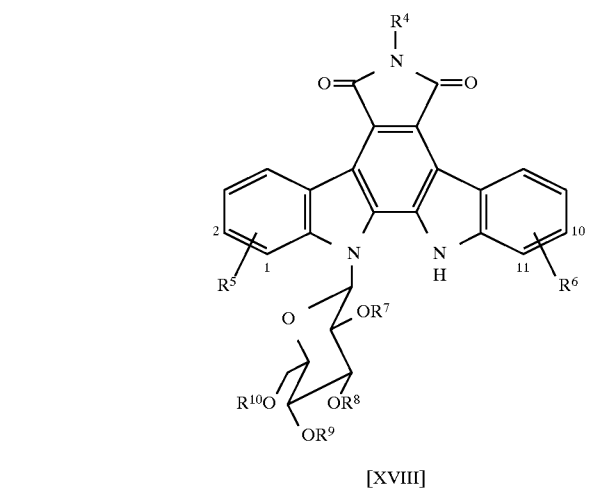
[XVIII]
Procedure D
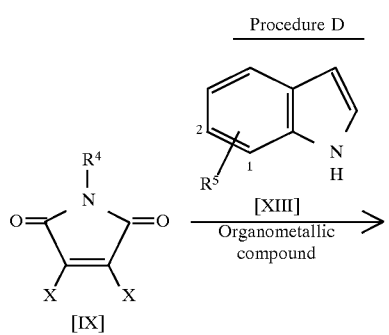
[IX]
-continued
Procedure D
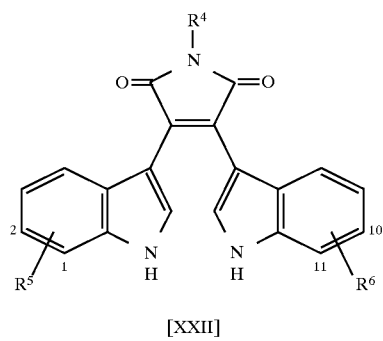
[XXII]
Procedure E
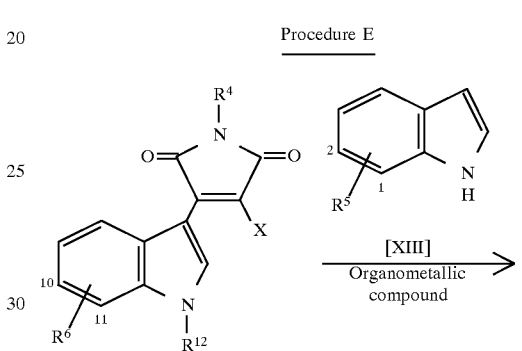
[XII]
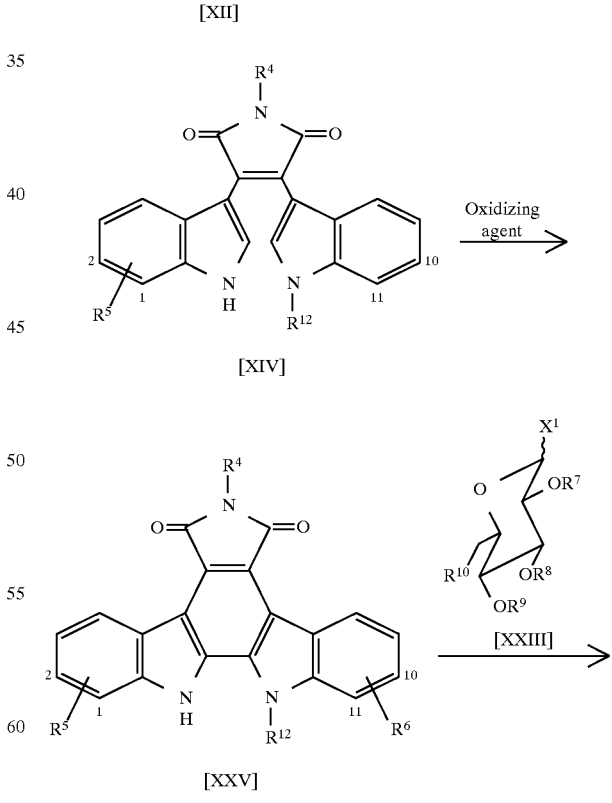
[XIV]
[XXV]

-continued
Procedure E

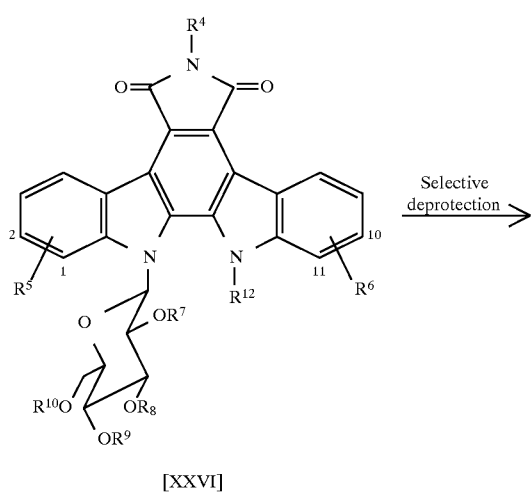

[XXVI]

Selective deprotection →

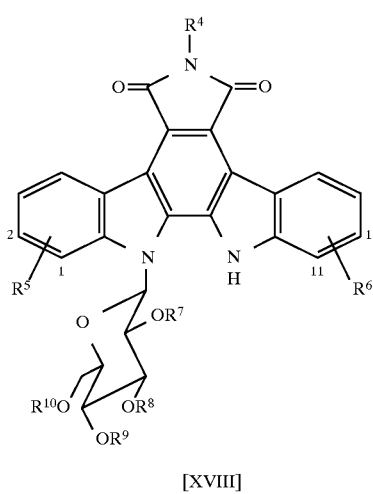

[XVIII]

The definitions of the symbols and terms used in procedures A to E and the claims given later are as follows.

In the general formulas, $R^1$ and $R^2$ each represent an OH group, provided that $R^1$ is located at the 1- or 2-position on the ring, $R^2$ is located at the 10- or 11-position on the ring, $R^2$ is located at the 11-position when $R^1$ is located at the 1-position, and $R^2$ is located at the 10-position when $R^1$ is located at the 2-position.

$R^3$ represents a lower alkyl group, a benzyloxymethyl group or an aralkyl group. The term "lower alkyl group" means straight-chain or branched alkyl groups of 1 to 6 carbon atoms, such as methyl, ethyl, propyl, sec-propyl, butyl, pentyl and hexyl. The term "aralkyl group" means aralkyl groups of 7 to 12 carbon atoms, such as benzyl, phenethyl and phenyl propyl.

$R^4$ represents a hydrogen atom, a lower alkyl group, a benzyloxymethyl group or an aralkyl group. The terms "lower alkyl group" and "aralkyl group" have the same meanings as described for $R^3$.

$R^5$ and $R^6$ each represent a protected OH group, provided that $R^5$ is located at the 1- or 2-position on the ring, $R^6$ is located at the 10- or 11-position on the ring, $R^6$ is located at the 11-position when $R^5$ is located at the 1-position, and $R^6$ is located at the 10-position when $R^5$ is located at the 2-position.

Usable protecting groups include, for example, benzyl, tolyl, p-methoxybenzyl and benzyloxymethyl groups.

$R^7$ to $R^{10}$ may be the same or different and each represent a protecting group for an OH group. Usable protecting groups include, for example, benzyl, tolyl, p-methoxybenzyl and benzyloxymethyl groups.

$R^{11}$ represents a hydrogen atom or a protecting group for the amino group of an indole skeleton. Usable protecting groups include, for example, lower alkoxycarbonyl carbonyl (such as tert-butoxycarbonyl and methyloxycarbonyl), benzyl, benzyloxymethyl, triisopropylsilyl, 2-trimethylsilylethyloxymethyl, mesyl and tosyl groups.

$R^{12}$ represents a protecting group for the amino group of an indole skeleton. Examples of the protecting group are the same as described above.

X represents a leaving group. Examples there-of of include chlorine, bromine and iodine atoms.

$X^1$ represents a leaving group. Examples thereof include halogen atoms such as chlorine, bromine and iodine atoms; and organic sulfonyloxy groups such as mesyl and tosyl.

The organometallic compound which is used to prepare a compound of the general formula [XI] or the like by reacting a maleimide compound of the general formula [IX] or the like with an indole compound of the general formula [X] or the like can be, for example, an alkyl lithium such as butyl lithium; lithium diisopropylamide; an alkali metal hexaalkyldisilazide such as lithium hexamethyldisilazide, sodium hexamethyldisilazide or potassium hexamethyldisilazide; or a Grignard reagent such as ethylmagnesium bromide or methylmagnesium chloride.

The Mitsunobu reaction is a reaction for forming a glycoside linkage by using an organic phosphine such as triphenylphosphine or tributylphosphine, and an azodicarboxylic acid derivative such as azodicarboxylic acid diethyl ester, azodicarboxylic acid di-tert-butyl ester, azodicarboxylic acid diisopropyl ester, azodicarboxylic acid di-N,N-dimethylamide or azodicarboxylic acid di-N-methylpiperazinamide (see Synthesis, I, 1981, pp. 1–28).

The oxidizing agent which is used to react a compound of the general formula [XVII] or the like having two indole skeletons with an oxidizing agent and thereby convert it to an indolopyrrolocarbazole compound of the general formula [XVIII] or the like can be 2,3-dichloro-5,6-dicyano-1,4-benzoquinone (hereinafter abbreviated as DDQ), $CuCl_2$, $Cu(OAc)_2$, $Cu(NO2)_2$, $PdCl_2$, $Pd(OAc)_2$, $Pd(CF_3COO)_2$ or the like.

Explanation of procedure A

As described above, the reaction of a maleimide compound of the general formula [IX] with an indole compound of the general formula [X] can be carried out with the aid of an alkali metal hexaalkyldisilazide such as lithium hexamethyldisilazide, or a Grignard reagent such as ethylmagnesium bromide. The solvents which can be used in this reaction include toluene, benzene, tetrahydrofuran (THF), dioxane, diethyl ether and the like.

The reaction temperature may usually range from –78° C. to 130° C. and preferably from –20° C. to 110° C.

A compound of the general formula [XII] can be prepared by introducing a protecting group for the amino group of the indole skeleton in a compound of the general formula [XI]. The protective agent used for this purpose can be a halide or acid anhydride corresponding to the aforesaid protecting group. Preferred examples thereof include di-tert-butyl dicarbonate and tert-butyloxycarbonyl chloride.

This reaction is preferably carried out in the presence of a base such as 4-N,N-dimethylaminopyridine. The solvents which can be used in this reaction include toluene, benzene, THF, dioxane, ether and the like. The reaction temperature may usually range from –78° C. to 100° C. and preferably from –25° C. to 25° C.

The preparation of a compound of the general formula [XIV] by reacting the compound of the general formula [XII] with a compound of the general formula [XIII] may be carried out in the same manner as described above for the reaction of the compound of the general formula [IX] with the compound of the general formula [XI].

The reaction of the compound of the general formula [XIV] with a compound of the general formula [XV] can be carried out according to the so-called Mitsunobu reaction. In this reaction, there may be used organic phosphines and azodicarboxylic acid derivatives as described above. Preferred examples of the organic phosphines include tributylphosphine and triphenylphosphine, and preferred examples of the azodicarboxylic acid derivatives include azodicarboxylic acid diethyl ester and azodicarboxylic acid diisopropyl ester.

As the reaction solvent, THF, dioxane, ether and the like may preferably be used. The reaction temperature may usually range from −78° C. to 50° C. and preferably from −40° C. to 20° C.

The deprotection of the amino group of an indole skeleton in a compound of the general formula [XVI] is preferably carried out under conditions which permit selective deprotection. For example, it is preferable to employ acidic or basic conditions which permit the tert-butoxycarbonyl, 2-trimethylsilylethoxymethyl or other group on the amino group to be selectively removed while retaining the other protecting groups.

For example, there may preferably be used acids such as trifluoroacetic acid and HF, and bases such as methylamine, tert-butoxypotassium and tetra-n-butyl ammonium fluoride.

A compound of the general formula [XVIII] can be prepared by oxidatively cyclizing a compound of the general formula [XVII]. The oxidizing agents which can be used in this reaction include, for example, DDQ, $CuCl_2$, $Cu(OAc)_2$, $Cu(NO_2)_2$ $PdCl_2$, $Pd(OAc)_2$ and $Pd(CF_3COO)_2$ as described above. As the reaction solvent, there may be used toluene, methylene chloride, dimethylformamide, dioxane, ether and the like. The reaction temperature may usually range from 0° C. to 100° C.

The removal of the protecting groups for the phenolic hydroxyl groups and the glycosyl group in the compound of the general formula [XVIII] can be carried out under acidic conditions or by well-known common hydrogenation reaction or the like.

A compound of the general formula [XX] can be prepared by reacting a compound of the general formula [XIX] with a base. The bases which can be used in this reaction include NaOH, KOH, $K_2CO_3$, $Na_2CO_3$, $NaHCO_3$ and the like. The solvents which can be used therein include water, methanol, ethanol, dimethylformamide and the like. The reaction temperature may usually range from 0° C. to the boiling point of the solvent.

A compound of the general formula [I] can be prepared by reacting the compound of the general formula [XX] with $H_2NNHCH(CH_2OH)_2$. The solvents which can be used in this reaction include methanol, ethanol, THF, dimethylformamide and the like. The reaction temperature may usually range from 0° C. to the boiling point of the solvent.

The amount of $H_2NNHCH(CH_2OH)_2$ used is usually in the range of 1 to 3 molar equivalents based on the compound [XX]. If necessary, this compound may be used in smaller or larger amounts.

Explanation of procedures B to E

The reaction of a compound of the general formula [XXIII] with a compound of the general formula [XXIV] in procedure C, and the reaction of a compound of the general formula [XXIII] with a compound of the general formula [XXV] in procedure E can be carried out in the presence of a base such as KOH, tert-BuOK, NaH, $K_2CO_3$ or lithium hexamethyldisilazide, in a solvent such as dimethylformamide, THF, toluene, methylene chloride or acetonitrile.

The reaction temperature may range from 0° C. to the boiling point of the solvent.

The other reactions in procedures B to E can be carried out under the same conditions as employed for the same types of reactions in procedure A.

A compound of the general formula [II] as claimed in claim 4 can be prepared, for example, by deprotecting a compound of the general formula [XXIV]. A compound of the general formula [XIX] can also be prepared by incubating a compound of the general formula [II] or the compound (28) together with a microorganism capable of glycosylating them (see Reference Examples 1 and 2).

After completion of each reaction, the desired product can be isolated and purified according to techniques widely known in the field of organic chemistry (e.g., precipitation, solvent extraction, recrystallization and chromatography). Moreover, $H_2NNHCH(CH_2OH)_2$ can be prepared, for example, according to the procedure described in Example 18.

Pharmacological tests

The compounds of the general formula [I], which are provided by the present invention, exhibit excellent antitumor effect as demonstrated by the following pharmacological tests.

(1) Growth-inhibiting activity (CTX) against various types of cancer cells

Measuring method

50 μl of a cell culture medium (RPMI-1640 medium containing 10% bovine fetal serum) containing $1×10^3$ mouse leukemia cells (P388), human gastric cancer cells (MKN-45), human pulmonary cancer cells (PC-13) or human rectal cancer cells (DLD-1) was pipetted into the wells of a 96-well microplate, and incubated at 37° C. under 5% $CO_2$ for 24 hours. Then, 50 μl of a test solution containing each test compound was added, and the culture medium was further incubated at 37° C. under 5% $CO_2$ for 72 hours. After 10 μl of 0.5% Thiazoyl Blue was added to the culture medium, an enzyme reaction was carried out by incubating the culture medium at 37° C. under 5% $CO_2$ for 2 hours. After the reaction was stopped by the addition of 20% sodium dodecyl sulfate (SDS), the culture medium was further incubated at 37° C. for 16 hours to dissolve the pigment so formed. Then, the absorbances at 560 nm were measured and compared with that obtained in a control group. The compound of the formula

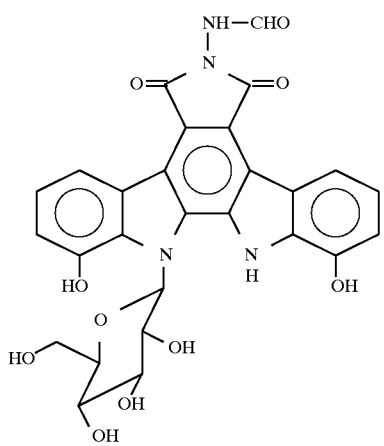

was used as the control compound. The results thus obtained are shown in Table 1.

TABLE 1

Growth-inhibiting activity against various types of cancer cells

| Test compound | CTX ($\mu$M) | | | |
|---|---|---|---|---|
| | P388 | MKN-45 | PC-13 | DLD-1 |
| Compound [I-A] | 0.037 | 0.29 | 0.34 | 0.67 |
| Compound [I-B] | 0.0020 | 0.011 | 0.035 | 0.10 |
| Control compound | 0.12 | 0.50 | 1.4 | 73 |

(2) Effect on human gastric cancer MKN-45

A MKN-45 solid tumor which had previously been grown by transplantation under the skin of a nude mouse was minced, and 3 mm cubes of the tumor were transplanted under the skin of mice used for this test. Starting from the time when the transplanted tumor grew to 0.3 cm$^3$, a treatment was carried out by injecting a dose of each test drug into the caudal vein of the mice, once a day, for 5 consecutive days and, after two days' pause, injecting the test drug for 5 days (treatment schedule: 5/w×2) or four times at intervals of 3 or 4 days (treatment schedule: 2/w×2). Twenty or thirty-two days after the start of the treatment, the larger diameter (L) and smaller diameter (W) of the tumor were measured, and its volume (V) was determined (V=½× L×W2). The degree of tumor growth inhibition was calculated from this volume, and the total dose at which the tumor growth was inhibited by 75% (GID$_{75}$, mg/kg) was determined. The results thus obtained are shown in Table 2.

TABLE 2

Effect of the compounds of the present invention on human gastric cancer MKN-45

| Test compound | Treatment schedule | GID$_{75}$ (mg/kg total) |
|---|---|---|
| Compound [I-A] | 5/w × 2 | 27 |
| Compound [I-B] | 2/w × 2 | 3.0 |
| Control compound | 5/w × 2 | 170 |

As shown by the results of the above-described pharmacological tests, the compounds provided by the present invention exhibit a more excellent antitumor effect than the control compound.

As is evident from the results of the above-described pharmacological tests, the compounds of the present invention exhibit an excellent antitumor effect and are hence useful as antitumor agents for the prophylaxis or treatment of diseases and, in particular, for the treatment of cancer. When the compounds of the present invention are used for these purposes, they may usually be combined with pharmaceutically acceptable carriers or excipients to make pharmaceutical preparations containing them in effective amounts.

The compounds of the present invention can be used as antitumor agents in various dosage forms. They include, for example, oral preparations such as tablets, capsules, powders, granules and waters; parenteral liquid preparations such as sterilized solutions and suspensions; suppositories; and ointments.

Solid preparations may be made by forming the compounds of the present invention directly into tablets, capsules, granules or powder. However, suitable additives may also be used in combination therewith. Such additives include sugars such as lactose and glucose; starches such as corn, wheat and rice; fatty acids such as stearic acid; inorganic salts such as magnesium aluminate metasilicate and anhydrous calcium phosphate; synthetic polymers such as polyvinyl pyrrolidone and polyalkylene glycol; fatty acid salts such as calcium stearate and magnesium stearate; alcohols such as stearyl alcohol and benzyl alcohol; synthetic cellulose derivatives such as methylcellulose, carboxymethylcellulose, ethylcellulose and hydroxypropylmethylcellulose; and other commonly used additives such as gelatin, talc, vegetable oils and gum arabic.

These solid preparations such as tablets, capsules, granules and powders may generally contain the active ingredient in an amount of 0.1 to 100% by weight and preferably 5 to 100% by weight.

In the case of liquid preparations, the compounds of the present invention may be formed into suspensions, syrups, injections or infusions with the aid of suitable additives commonly used in liquid preparations, such as water, alcohols and vegetable oils (e.g., soybean oil, peanut oil and sesame oil).

Especially when they are parenterally administered by intramuscular, intravenous or subcutaneous injection, suitable solvents include, for example, distilled water for injection, an aqueous solution of lidocaine hydrochloride (for intramuscular injection), physiological saline, an aqueous glucose solution, ethanol, polyethylene glycol, liquids for intravenous injection (e.g., aqueous solutions of citric acid and sodium citrate) and electrolyte solutions (for intravenous drip infusion and intravenous injection), as well as mixtures thereof.

These injections may be prepared not only in previously dissolved form, but also in the form of a powder or mixture with suitable additives for dissolution prior to use. These injections may usually contain the active ingredient in an amount of 0.1 to 10% by weight and preferably 1 to 5% by weight.

Liquid preparations for oral administration, such as suspensions and syrups, may usually contain the active ingredient in an amount of 0.5 to 10% by weight.

The preferred dosages of the compounds of the present invention may vary according to the type of the compound used, the type of the composition prepared, the frequency of use, the site to be treated, the severity of symptoms, the age of the patient, the diagnosis made by the doctor, the type of the tumor, and the like. By way of example, their daily dose for adults may be in the range of 1 to 800 mg for oral administration, and in the range of 0.1 to 500 mg for parenteral administration and preferably for intravenous injection. These daily doses may be given at a time or in 2 to 5 divided doses, depending on the method of administration and the severity of symptoms. Alternatively, they may be administered intermittently, for example, every second or third day.

The present invention is more specifically explained with reference to the following examples. However, it is to be understood that the present invention is not limited thereto.

EXAMPLE 1

Preparation of the compound represented by the formula

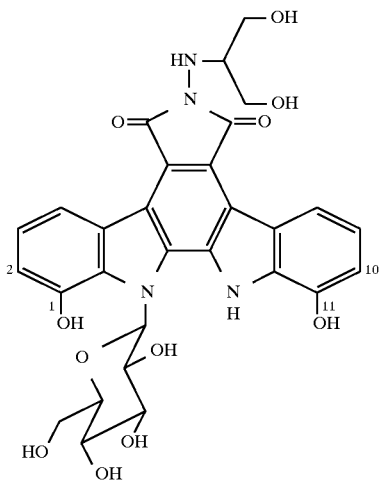

[1-A]

This compound was prepared according to a method comprising the following steps 1) to 9).

1) Preparation of the compound represented by the formula

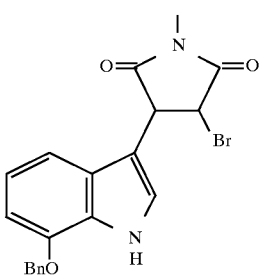

(1)

wherein Bn represents a benzyl group and the same will apply hereinafter.

15 g of 7-benzyloxyindole was dissolved in 150 ml of THF, and 161.3 ml of lithium hexamethyldisilazide (as a 1M solution in THF) was added thereto. After this mixture was stirred under an atmosphere of nitrogen at 0° C. for 30 minutes, 180 ml of a THF solution containing 18.1 g of 2,3-dibromo-N-methylmaleimide was added dropwise thereto over a period of 10 minutes.

After completion of the addition, the resulting mixture was stirred at 0° C. for 0.5 hour. The reaction mixture was poured into 1 liter of 2N hydrochloric acid and extracted with 2 liters of ethyl acetate. The organic layer was washed with a saturated aqueous solution of sodium hydrogen carbonate and then a saturated aqueous solution of sodium chloride, dried and concentrated. The resulting residue was recrystallized from ethyl acetate-hexane to obtain 26.9 g of the desired compound (1) (in a 97% yield).

HRMS (m/z): found 410.0273, calcd 410.0248 [as $C_{20}H_{15}N_2O_3Br$]

IR (KBr, $cm^{-1}$): 1705, 1628, 1576, 1433, 1383, 1259, 1247, 1076, 762, 739.

$^1$H-NMR (300 MHz, $CDCl_3$, δ ppm): 9.03(1H, brs), 7.94(1H, d, J=3.0 Hz), 7.64(1H, d, J=8.0 Hz), 7.30–7.53(5H, m), 7.15(1H, t, J=8.0 Hz), 6,82(1H, d, J=8.0 Hz), 5.22(2H, s), 3.16(3H, s).

2) Preparation of the compound represented by the formula

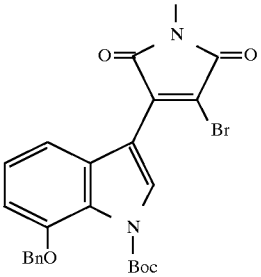

(2)

wherein Boc represents a tert-butoxycarbonyl group and the same will apply hereinafter.

29 g of the compound (1) obtained in Example 1-1), 169 g of di-tert-butyl dicarbonate and 136 mg of 4-N,N-dimethylaminopyridine were dissolved in 200 ml of THF, and this solution was stirred at room temperature for 1 hour. After the reaction mixture was concentrated, the resulting residue was purified by silica gel chromatography (chloroform) and then recrystallized from chloroform-ethyl acetate-hexane to obtain 32.9 g of the desired compound (2) (in a 92% yield).

IR (KBr, $cm^{-1}$): 1765, 1712, 1438, 1369, 1261, 1228, 1149, 739.

HRMS (m/z): found 510.0815, calcd 510.0790 [as $C_{25}H_{23}N_2O_5Br$]

$^1$H-NMR (300 MHz, $CDCl_3$, δ ppm): 8.04(1H, s), 7.20–7.62(7H, m), 6.95(1H, d, J=7.9 Hz), 5.23(2H, s), 3.18(3H, s), 1.53(9H, s).

3) Preparation of the compound represented by the formula

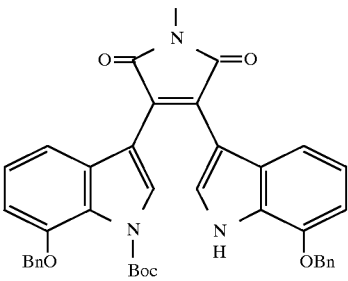

(3)

107.2 mg of 7-benzyloxyindole was dissolved in 3 ml of THF, and 0.48 ml of lithium hexamethyldisilazide (as a 1M solution in THF) was added thereto. After this mixture was stirred under an atmosphere of nitrogen at 0° C. for 15 minutes, 2 ml of a THF solution containing 102.2 mg of the compound (2) obtained in Example 1-2) was added dropwise thereto over a period of 20 minutes. After completion of the addition, the resulting mixture was stirred at room temperature for 0.5 hour. The reaction mixture was poured into 10 mL of 2N hydrochloric acid and extracted with 30 mL of ethyl acetate. The organic layer was washed with water, a saturated aqueous solution of sodium hydrogen carbonate and then a saturated aqueous solution of sodium chloride, dried and concentrated. The resulting residue was purified by silica gel chromatography (hexane-ethyl acetate=4:1) to obtain 112.7 mg of the desired compound (3) (in a 86% yield).

HRMS (m/z): found 653.2529, calcd 653.2526 [as $C_{40}H_{35}N_3O_6$]

IR (KBr, cm$^{-1}$) 1759, 1734, 1579, 1498, 1430, 1261, 1217, 1149, 752, 733.

$^1$H-NMR (300 MHz, CDCl$_3$, δ ppm): 8.78(1H, brs), 7.90(1H, s), 7.75(1H, s), 7.29–7.52(10H, m), 6.58–6.82(6H, m), 5.17(2H, s), 5.15(2H, S), 3.19(3H, s), 1.53(9H, s).

4) Preparation of the compound represented by the formula

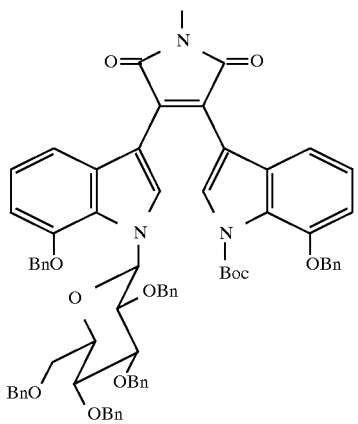

(4)

300mg of the compound (3) obtained in Example 1-3), 746.2 mg of 2,3,4,6-O-tetrabenzyl-D-glucopyranose and 543 mg of triphenylphosphine were dissolved in 15 ml of THF, and 0.419 ml of azodicarboxylic acid diisopropyl ester was added thereto at −78° C. This mixture was stirred for 3 hours, during which time its temperature was gradually raised to room temperature. The reaction mixture was partitioned between 40 ml of ethyl acetate and 20 ml of 2N hydrochloric acid. The organic layer was washed with water, a saturated aqueous solution of sodium hydrogen carbonate, water and then a saturated aqueous solution of sodium chloride, dried and concentrated. The resulting residue was purified by silica gel chromatography (toluene-ethyl acetate =50:1) to obtain 459.3 mg of the desired compound (4) (in a 85% yield).

HRMS (m/z): found 1175.4950, calcd 1175.4932 [as $C_{74}H_{69}N_3O_{11}$]

IR (KBr, cm$^{-1}$): 1759, 1701, 1579, 1454, 1440, 1384, 1358, 1259, 1232, 1149, 1087, 752, 735, 662.

$^1$H-NMR (300 MHz, CDCl$_3$, δ ppm): 8.19(1H, s), 7.91 (1H, s), 7.45(2H, d, J=6.6 Hz), 6.96–7.39(25H, m), 6.54–6.71(7H, m), 6.48(2H, dd, J=1.6, 8.5 Hz), 6.43(1H, d, J=8.9 Hz), 5.13(2H, s), 5.02(1H, d, J=11.4 Hz), 4.90(1H, d, J=10.7 Hz), 4.84(1H, d, J=10.8 Hz), 4.83(1 Hd, J=11.4 Hz), 4.80(1H, d, J=10.8 Hz), 4.60(1H, d, J=12.7 Hz), 4.59(1H, d, J=10.8 Hz), 4.53(1H, d, J=11.4 Hz), 4.39(1H, d, J=9.9 Hz), 3.80(1H, t, J=8.9 Hz), 3.64–3.76(4H, m), 3.56(1H, t, J=9.1 Hz), 3.38–3.46(1H, m), 3.19(3H, s), 1.53(9H, s).

5) Preparation of the compound represented by the formula

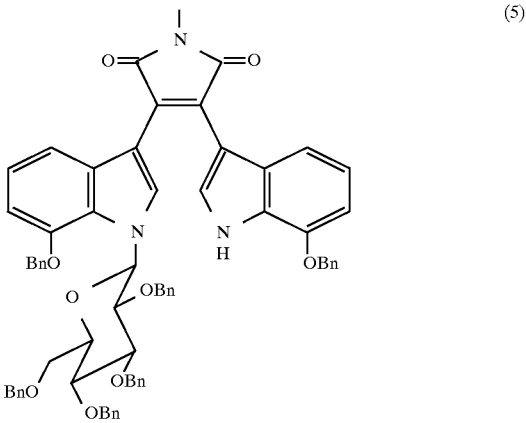

(5)

459.3 mg of the compound (4) obtained in Example 1-4) was dissolved in 20 ml of methylamine (as a 40% solution in methanol), and this solution was stirred at room temperature for 30 minutes. After the reaction mixture was concentrated, the resulting residue was purified by silica gel chromatography (hexane-ethyl acetate=4:1) to obtain 395.2 mg of the desired compound (5) (in a 94% yield).

HRMS (m/z): found 1075.4445, calcd 1075.4408 [as $C_{69}H_{61}N_3O_9$]

IR (KBr, cm$^{-1}$): 1697, 1577, 1569, 1497, 1454, 1436, 1257, 1083, 752, 753, 696.

$^1$H-NMR (300 MHz, CDCl$_3$, δ ppm): 8.61(1H, brs), 8.07(1H, s), 7.56(1H, d, J=2.7 Hz), 6.95–7.50(27H, m), 6.85(1H, d, J=7.2 Hz), 6.40–6.70(9H, m), 5.13(2H, s), 5.06(1H, d, J=11.1 Hz), 4.91(1H, d, J=11.1 Hz), 4.90(1H, d, J=11.1 Hz), 4.84(1H, d, J=9.6 Hz), 4.80(1H, d, J=11.1 Hz), 4.48–4.62(3H, m), 4.41(1H, d, J=10.3 Hz), 3.64–3.83(4H, m), 3.57(2H, t, J=8.97 Hz), 3.40–3.48(1H, m), 3.18(3H, m).

6) Preparation of the compound represented by the formula

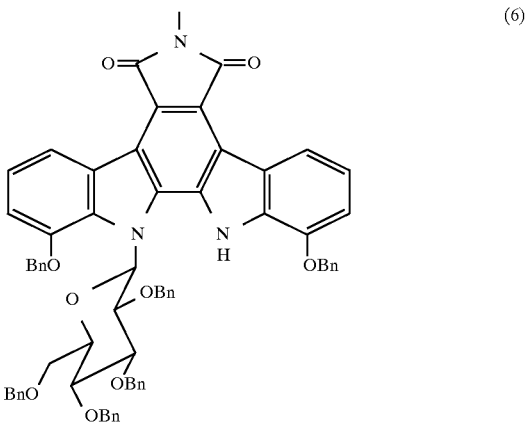

(6)

52 mg of the compound (5) obtained in Example 1-5) was dissolved in 2.5 ml of DMF, and 49.9 mg of palladium triflouroacetate was added thereto. This mixture was stirred at 90° C. for 3 hours. The reaction mixture was partitioned between ethyl acetate and 2N hydrochloric acid. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate =4:1) to obtain 26 mg of the desired compound (6) (in a 50% yield).

HRMS (m/z): found 1073.4269, calcd 1073.4251 [as $C_{69}H_{59}N_3O_9$]

IR (KBr, cm$^{-1}$) 2617, 1699, 1581, 1377, 1257, 1097, 1072, 754, 696.

$^1$H-NMR (300 MHz, CDCl$_3$, δ ppm): 10.55(1H, s), 9.08 (1H, d, J=7.3 Hz), 8.87(1H, d, J=8.3 Hz), 6.90–7.51(31H, m), 6.86(2H, t, J=7.6 Hz), 6.17(2H, d, J=6.9 Hz), 5.30(1H, d, J=11.5 Hz), 5.20(2H, d, J=11.5 Hz), 5.14(1H, d, J=11.5 Hz), 4.73(1H, d, J=10.9 Hz), 4.64(1H, d, J=10.9 Hz), 4.59(1H, d, J=11.0 Hz), 4.57(1H, d, J=13.1 Hz), 4.52(1H, d, J=13.1 Hz), 4.10(1H, d, J=11.0 Hz), 4.00(1H, t, J=9.1 Hz), 3.83(1H, d, J=9.6 Hz), 3.52–3.76(5H, m), 3.49(3H, s), 2.95(1H, d, J=9.6 Hz).

7) Preparation of the compound represented by the formula

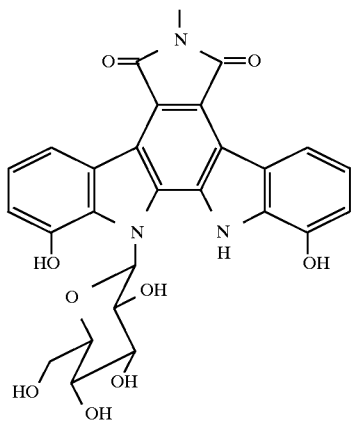

(7)

270 mg of the compound (6) obtained in Example 1-6) was dissolved in 15 ml of chloroform-methanol (1:1), and a catalytic amount of palladium black was added thereto. This mixture was stirred under an atmosphere of hydrogen for 4 hours. After the catalyst was filtered off, the filtrate was concentrated. The resulting residue was recrystallized from methanol-chloroform-hexane to obtain 130 mg of the desired compound (7) (in a 98% yield).

HRMS (m/z): found 533.1419, calcd 533.1434 [as $C_{27}H_{23}N_3O_9$]

IR (KBr, cm$^{-1}$): 3371, 1741, 1638, 1587, 1577, 1387, 1321, 1261, 1238, 1081, 754.

$^1$H-NMR (300 MHz, DMSO-d$_6$, δ ppm): 10.89(1H, s), 10.34(1H, s), 9.95(1H, s), 8.71(1H, d, J=7.7 Hz), 8.53(1H, d, J=7.7 Hz), 7.18(2H, t, J3=7.7 Hz), 7.05(1H, d, J=9.1 Hz), 7.01(1H, d, J=7.7 Hz), 6.99(1H, d, J=7.7 Hz), 4.50–5.80(4H, br), 3.95–4.08(2H, m), 3.58–3.80(3H, m), 3.39(1H, dd, J=8.6, 9.1 Hz), 3.18(3H, s).

8) Preparation of the compound represented by the formula

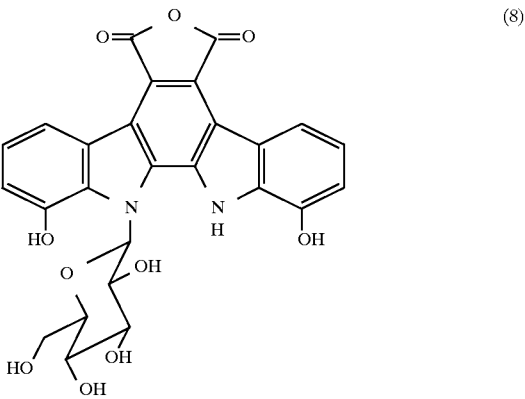

(8)

70 mg of the compound (7) obtained in Example 1-7) was dissolved in 2 ml of a 10% aqueous solution of potassium hydroxide, and this solution was stirred at room temperature for 0.5 hour. The reaction mixture was neutralized by the addition of 1 ml of 2N hydrochloric acid, and then extracted with methyl ethyl ketone-ethyl acetate (1:1). The organic layer was washed with a saturated aqueous solution of sodium chloride, dried and concentrated. The resulting residue was washed with dichloromethane to obtain 65 mg of the title compound (8) (in a 95% yield).

HRMS (m/z): found 520.1117, calcd 520.1118 [as $C_{26}H_{20}N_2O_{10}$]

IR (KBr, cm$^{-1}$) 3353, 1816, 1743, 1587, 1388, 1249, 1072, 800, 748, 609.

$^1$H-NMR (300 MHz, DMSO-d$_6$, δ ppm): 11.11(1H, s), 10.52(1H, s), 10.13(1H, s), 8.51(1H, d, J=7.6 Hz), 8.36(1H, d, J=7.6 Hz), 7.40(1H, d, J=7.8 Hz), 7.20(1H, d, J=7.8 Hz), 7.09(1H, d, J=8.0 Hz), 7.06(2H, dd, J=7.6, 7.8 Hz), 5.32(1H, dd, J=4.9, 5.1 Hz), 5.24(1H, d, J=5.4 Hz), 4.95(1H, d, J=4.6 Hz), 3.95–4.10(2H, m), 3.76(1H, m), 3.56–3.70(2H, m), 3.42(1H, m).

9) 100 mg of the compound (8) obtained in Example 1-8) was dissolved in 10 ml of DMF, and 61 mg of 2-hydrazino-1,3-propanediol was added thereto. This mixture was stirred at 80° C. for 1 hour. After the reaction mixture was concentrated, the resulting residue was developed with Sephadex LH-20 and eluted with methanol to obtain 89 mg of the title compound [I-A] (in a 77% yield).

HRMS (m/z): found 609.1826, calcd 609.1833 [as $C_{29}H_{28}N_4O_{11}$]

IR (KBr, cm$^{-1}$): 3309, 1695, 1567, 1540, 1521, 1456, 1417, 1398, 1087, 609.

$^1$H-NMR (300 MHz, DMSO-d$_6$, δ ppm): 10.91(1H, brs), 10.30(1H, brs), 9.90(1H, s), 8.70(1H, d, J=8.0 Hz), 8.52(1H, d, J=7.9 Hz), 7.16–7.21(2H, m), 6.98–7.05(3H, m), 5.59(1H, d, J=2.3 Hz), 5.41(1H, d, J=5.7 Hz), 5.20–5.40(2H, m), 5.20(1H, d, J=5.3 Hz), 4.90(1H, br), 4.50–4.60(3H, m), 3.98–4.15(2H, m), 3.35–3.80(7H, m).

EXAMPLE 2

Preparation of the compound represented by the formula

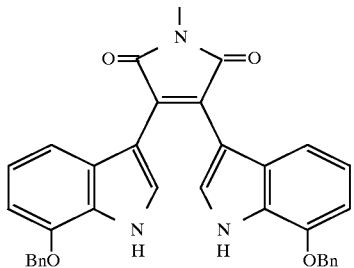
(9)

69 mg of the compound (3) obtained in Example 1-3) was dissolved in 1 ml of methylamine (as a 40% solution in methanol), and this solution was stirred at room temperature for 10 minutes. After the reaction mixture was concentrated, the resulting residue was recrystallized from ethyl acetate-hexane to obtain 55.2 mg of the desired compound (9) (in a 95% yield).

HRMS (m/z): found 553.1982, calcd 553.2002 [as $C_{35}H_{27}N_3O_4$]

IR (KBr, cm$^{-1}$): 1691, 1577, 1531, 1423, 1384, 1259, 1083, 752, 715, 694.

$^1$H-NMR (300 MHz, CDCl$_3$, δ ppm): 8.73(2H, brs), 7.69(2H, d, J=2.1 Hz), 7.30–7.49(10H, m), 6.60–6.75(6H, m), 5.16(4H, s), 3.17(3H, s).

EXAMPLE 3

Preparation of the compound represented by the formula

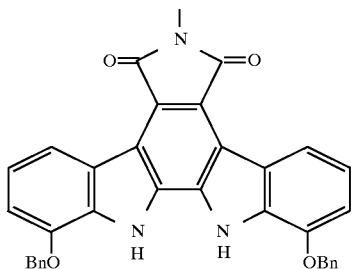
(10)

30 mg of the compound (9) obtained in Example 2 and 49.9 mg of palladium triflouroacetate were added, and this mixture was stirred at 90° C. for 0.5 hour. The reaction mixture was partitioned between ethyl acetate and 2N hydrochloric acid. The organic layer was washed with water, a saturated aqueous solution of sodium hydrogen carbonate, water and then a saturated aqueous solution of sodium chloride, dried and concentrated. The resulting residue was developed with Sephadex LH-20 and eluted with methanol to obtain 14.6 mg of the desired compound (10) (in a 49% yield).

HRMS (m/z): found 551.1839, calcd 551.1845 [as $C_{35}H_{25}N_3O_4$]

IR (KBr, cm$^{-1}$): 1742, 1695, 1684, 1577, 1406, 1377, 1251, 1103, 776, 737, 696.

$^1$H-NMR (300 MHz, DMSO-d$_6$, δ ppm): 11.67(2H, s), 8.52–8.55(2H, m), 7.62(4H, d, J=7.1 Hz), 7.46(4H, t, J=7.1 Hz), 7.40(2H, d, J=7.1 Hz), 7.23–7.28(4H, m), 5.37(4H, s), 3.30(3H, s).

EXAMPLE 4

Preparation of the compound represented by the formula

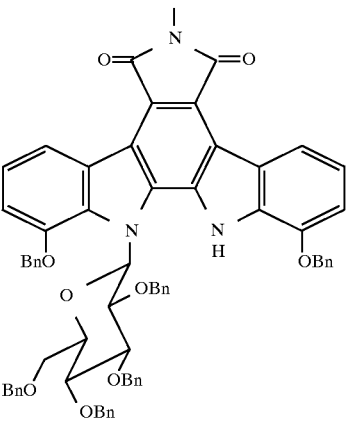
(6)

360 mg of potassium hydroxide and 2.2 g of sodium sulfate were suspended in 40 ml of acetonitrile, and 483 mg of the compound (10) obtained in Example 3 was added thereto. After this mixture was stirred at room temperature for 0.5 hour, 12 ml of an acetonitrile solution containing 1.06 g of 1-chloro-2,3,4,6-tetra-O-benzyl-D-glucopyranoside was added dropwise thereto. After the resulting mixture was stirred at room temperature overnight, the reaction mixture was poured into 50 ml of 2N hydrochloric acid and extracted with 200 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=10:1, toluene-ethyl acetate=90:1) to obtain 840 mg of the desired compound (6) (in a 90% yield).

Its property data agreed with those obtained in Example 1-6).

EXAMPLE 5

Preparation of the compound represented by the formula

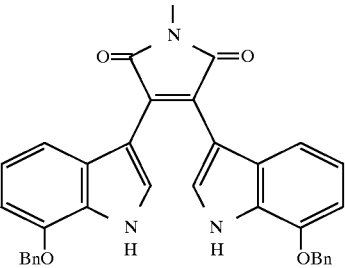
(9)

2.24 ml of ethylmagnesium bromide (as a 1M solution in THF) was dissolved in 2.2 ml of toluene, and 500 mg of 7-benzyloxyindole was added thereto at 45° C. After this mixture was heated to 130° C., 2.8 ml of a toluene solution containing 201.7 mg of 2,3-dibromo-N-methylmaleimide was added thereto, followed by stirring at 130° C. for 4 hours. The reaction mixture was poured into 5 ml of 2N hydrochloric acid and extracted with 20 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=4:1 to 2:1) to obtain 156 mg of the desired compound (9) (in a 38% yield).

Its property data agreed with those obtained in Example 2.

EXAMPLE 6

Preparation of the compound [I-B] represented by the formula

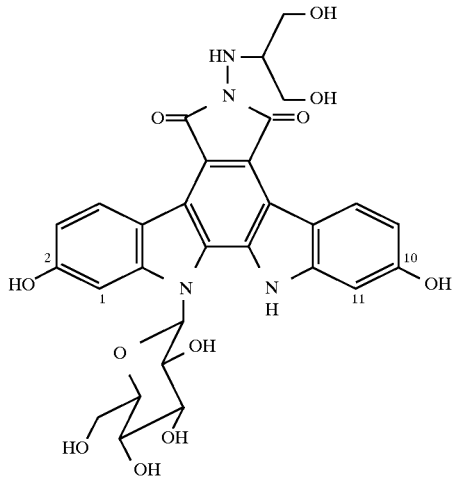

This compound was prepared according to a method comprising the following steps 1) to 9).

1) Preparation of the compound represented by the formula

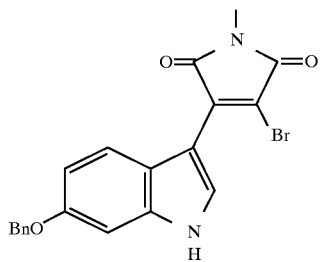

284 g of 6-benzyloxyindole was dissolved in 3 liters of THF, and 2.7 liters of lithium hexamethyldisilazide (as a 1M solution in THF) was added thereto. After this mixture was stirred under an atmosphere of nitrogen at −10° C. for 45 minutes, 3 liters of a THF solution containing 340 g of 2,3-dibromo-N-methyl-maleimide was added dropwise thereto over a period of 1 hour.

After completion of the addition, the resulting mixture was stirred at 0° C. for 15 minutes. The reaction mixture was poured into 10 liters of 2N hydrochloric acid and extracted with 30 liters of ethyl acetate. The organic layer was washed with a saturated aqueous solution of sodium hydrogen carbonate and then a saturated aqueous solution of sodium chloride, dried and concentrated. The resulting residue was recrystallized from methanol to obtain 482 g of the desired compound (11) (in a 93% yield).

HRMS (m/z): found 410.0292, calcd 410.0266 [as $C_{20}H_{15}N_2O_3Br$]

IR (KBr, $cm^{-1}$): 3330, 3318, 1762, 1701, 1606, 1511, 1450, 1165, 1135, 1041, 794.

$^1$H-NMR (300 MHz, $CDCl_3$, δ ppm): 8.60(1H, brs), 7.96(1H, d, J=8.1 Hz), 7.94(1H, d, J=2.5 Hz), 7.33–7.47(5H, m), 7.00(1H, dd, J=2.5, 8.8 Hz), 6.97(1H, d, J=2.5 Hz), 5.13(2H, s), 3.16(3H, s).

2) Preparation of the compound represented by the formula

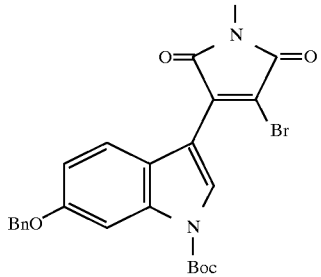

1.00 g of the compound (11) obtained in Example 6-1), 637 mg of di-tert-butyl dicarbonate and 3 mg of 4-N,N-dimethylaminopyridine were dissolved in 200 ml of THF, and this solution was stirred at room temperature for 1 hour. After the reaction mixture was concentrated, the resulting residue was recrystallized from ethyl acetate-hexane to obtain 1.18 g of the desired compound (12) (in a 96% yield).

IR (KBr, $cm^{-1}$): 1740, 1714, 1614, 1527, 1487, 1443, 1373, 1227, 1153.

HRMS (m/z): found 510.0771, calcd 510.0791 [as $C_{25}H_{23}N_2O_5Br$]

$^1$H-NMR (300 MHz, $CDCl_3$, δ ppm): 8.10(1H, s), 7.91 (1H, d, J=2.3 Hz), 7.73(1H, d, J=8.9 Hz), 7.34–7.50(5H, m), 7.03(1H, dd, J=2.3, 8.5 Hz), 5.16(2H, s), 3.18(3H, s), 1.68(9H, s).

3) Preparation of the compound represented by the formula

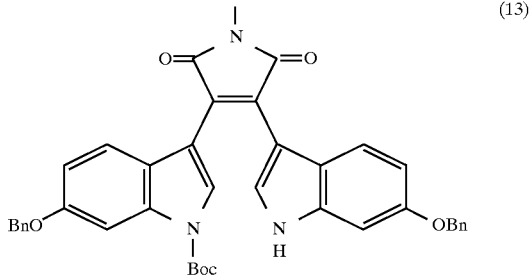

218.4 mg of 6-benzyloxyindole was dissolved in 20 ml of THF, and 2.35 ml of lithium hexamethyldisilazide (as a 1M solution in THF) was added thereto. After this mixture was stirred under an atmosphere of nitrogen at 0° C. for 15 minutes, 10 ml of a THF solution containing 500 mg of the compound (12) obtained in Example 6-2) was added dropwise thereto over a period of 10 minutes. After completion of the addition, the resulting mixture was stirred at room temperature for 0.5 hour. The reaction mixture was poured into 100 mL of 2N hydrochloric acid and extracted with 400 mL of ethyl acetate. The organic layer was washed with water, a saturated aqueous solution of sodium hydrogen carbonate and then a saturated aqueous solution of sodium chloride, dried and concentrated. The resulting residue was recrystallized from toluene-hexane to obtain 580 mg of the desired compound (13) (in a 91% yield).

HRMS (m/z): found 653.2556, calcd 653.2526 [as $C_{40}H_{35}N_3O_6$]

IR (KBr, $cm^{-1}$): 1740, 1701, 1646, 1623, 1543, 1445, 1155.

$^1$H-NMR (300 MHz, $CDCl_3$, δ ppm): 8.41(1H, brs), 7.97(1H, s), 7.84(1H, brs), 7.68(1H, brs), 7.16–7.43(10H, m), 6.98(1H, d, J=9.2 Hz), 6.85(1H, brs), 6.74(1H, d, J=9.2 Hz), 6.58(1H, d, J=9.2 Hz), 6.52(1H, d, J=9.2 Hz), 5.05(2H, s), 5.02(2H, s), 3.19(3H, s), 1.67(9H, s).

4) Preparation of the compound represented by the formula

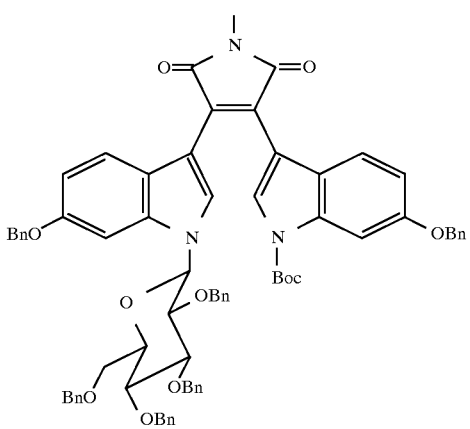

(14)

50 mg of the compound (13) obtained in Example 6-3), 186 mg of 2,3,4,6-O-tetrabenzyl-D-glucopyranose and 90 mg of triphenylphosphine were dissolved in 3 ml of THF, and 0.054 ml of azodicarboxylic acid diethyl ester was added thereto at 0° C. . This mixture was stirred for 1 hour. The reaction mixture was partitioned between 40 ml of ethyl acetate and 20 ml of 2N hydrochloric acid. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=4:1) to obtain 36.4 mg of the desired compound (14) (in a 62% yield).

HRMS (m/z): found 1175.4955, calcd 1175.4932 [as $C_{74}H_{69}N_3O_{11}$]

IR (KBr, cm$^{-1}$): 2360, 1736, 1701, 1616, 1543, 1489, 1454, 1363, 1219, 1153.

$^1$H-NMR (300 MHz, CDCl$_3$, δ ppm): 8.03(1H, s), 7.95 (1H, s), 7.78–7.82(1H, m), 7.04–7.38(30H, m), 6.84(1H, d, J=8.7 Hz), 6.76–6.84(1H, m), 6.79(1H, d, J=8.9 Hz), 6.32 (1H, dd, J=2.2, 8.9 Hz), 6.28(1H, dd, J=2.4, 8.7 Hz), 5.33(1H, d, J=8.7 Hz), 4.82–4.94(7H, m), 4.67(1H, d, J=10.6 Hz), 4.63(1H, d, J=12.1 H), 4.55(1H, d, J=12.1 Hz), 4.10 (1H, d, J=10.2 Hz), 3.69–3.95(6H, m), 3.40(1H, d, J=10.2 Hz), 3.20(3H, s), 1.66(9H, s).

5) Preparation of the compound represented by the formula

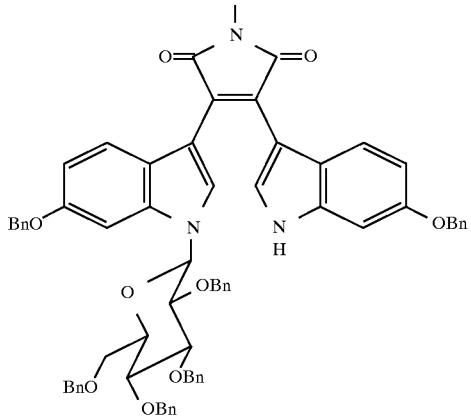

(15)

14.1 mg of the compound (14) obtained in Example 6-4) was dissolved in 5 ml of methylamine (as a 40% solution in methanol), and this solution was stirred at room temperature for 30 minutes. After the reaction mixture was concentrated, the resulting residue was purified by silica gel chromatography (hexane-ethyl acetate=7:3) to obtain 12.3 mg of the desired compound (15) (in a 96% yield).

HRMS (m/z): found 1075.4392, calcd 1075.4408 [as $C_{69}H_{61}N_3O_9$]

IR (KBr, cm$^{-1}$): 3311, 3030, 2927, 1697, 1621, 1533, 1454, 1385, 1159, 1093.

$^1$H-NMR (300 MHz, CDCl$_3$, δ ppm): 8.29(1H, d,J=2.7 Hz), 7.96(1H, s), 7.52(1H, d, J=2.7 Hz), 7.19–7.40(25H, m), 7.03–7.19(5H, m), 6.78–6.84(3H, m), 6.67(1H, d, J=8.8 Hz), 6.45(1H, dd, J=2.2, 8.8 Hz), 6.34(1H, dd, J=2.2, 8.8 Hz), 5.34(1H, d, J=8.7 Hz), 4.82–4.94(7H, m), 4.67(1H, d, J=10.7 Hz), 4.62(1H, d, J=12.2 Hz), 4.53(1H, d, J=12.2 Hz), 4.12(1H, d, J=10.2 Hz), 3.67–3.98(7H, m), 3.18(3H, m).

6) Preparation of the compound represented by the formula

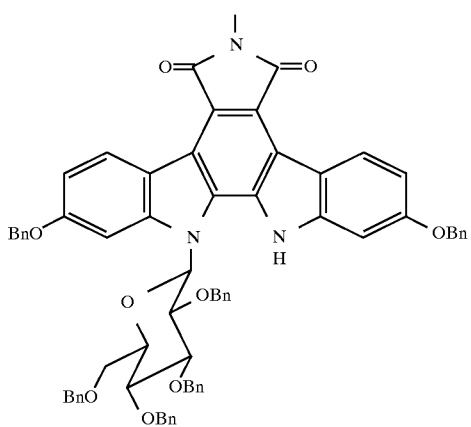

(16)

52 mg of the compound (15) obtained in Example 6-5), 26.8 mg of copper(II) chloride and 50 mg of molecular sieve were dissolved in 1 ml of methyl ethyl ketone, and this solution was stirred at room temperature for 2 hours. After the reaction mixture was filtered through celite, the filtrate was concentrated. The resulting residue was purified by silica gel chromatography (dichloromethane) to obtain 42 mg of the desired compound (16) (in a 84% yield).

HRMS (m/z): found 1073.4237, calcd 1073.4251 [as $C_{69}H_{59}N_3O_9$]

IR (KBr, cm$^{-1}$): 3311, 3030, 2927, 1697, 1621, 1533, 1454, 1385, 1159, 1093.

$^1$H-NMR (300 MHz, CDCl$_3$, δ ppm): 10.6(1H, s), 9.24 (1H, d, J=9.5 Hz), 9.13(1H, d, J=9.5 Hz), 7.07–7.50(29H, m), 6.98–7.03(1H, m), 6.83–6.91(2H, m), 6.18–6.22(2H, m), 5.84(1H, d, J=8.9 Hz), 5.12–5.22(2H, m), 5.18(1H, d, J=11.5 Hz), 5.08(1H, d, J=11.5 Hz), 4.97(1H, d, J=10.7 Hz), 4.89(1H, d, J=10.7 Hz), 4.84(1H, d, J=10.7 Hz), 4.74(1H, d, J=13.0 Hz), 4.67(1H, d, J=10.7 Hz), 4.56(1H, d, J=13.0 Hz), 4.32(1H, dd, J=9.6, 9.6 Hz), 3.98–4.07(2H, m), 3.82–3.97 (3H, m), 3.79(1H, dd, J=2.7, 10.2 Hz), 3.33(3H, s), 3.00(1H, d, J=9.7 Hz).

7) Preparation of the compound represented by the formula

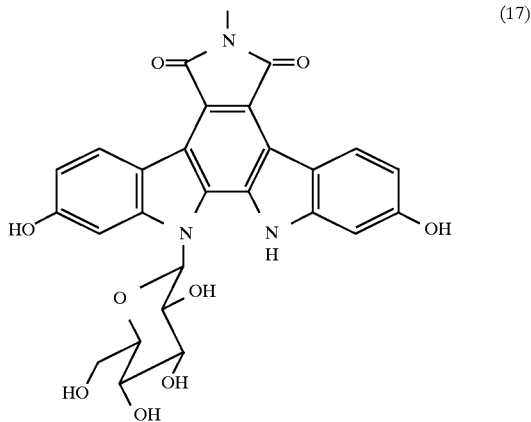

(17)

100 mg of the compound (16) obtained in Example 6-6) was dissolved in 6 ml of chloroform-methanol (2:1), and a catalytic amount of palladium black was added thereto. This mixture was stirred under an atmosphere of hydrogen for 2 hours. After the catalyst was filtered off, the filtrate was concentrated. The resulting residue was crystallized from methanol-acetone-ethyl acetate-hexane, developed with Sephadex LH-20, eluted with chloroform-methanol-ethanol-tetrahydrofuran (5:2:2:1), and recrystallized from acetone-methanol-hexane to obtain 43.8 mg of the desired compound (17) (in a 88% yield).

HRMS (m/z): found 533.1429, calcd 533.1434 [as $C_{27}H_{23}N_3O_9$]

IR (KBr, cm$^{-1}$): 3328, 1733, 1683, 1678, 1540, 1417, 1126, 1081, 611.

$^1$H-NMR (300 MHz, DMSO-d$_6$, δ ppm): 11.20(1H, s), 9.76(1H, s), 9.74(1H, s), 8.88(1H, d, J=8.6 Hz), 8.80(1H, d, J=8.6 Hz), 7.18(1H, d, J=2.1 Hz), 6.99(1H, d, J=2.1 Hz), 6.82(1H, dd, J=2.1, 8.6 Hz), 6.80(1H, dd, J=2.1, 8.6 Hz), 5.97(1H, d, J=8.9 Hz), 5.86(1H, t, J=4.0 Hz), 5.33(1H, d, J=4.9 Hz), 5.12(1H, d, J=4.3 Hz), 4.94(1H, d, J=5.2 Hz), 4.02(1H, dd, J=3.0, 10.7 Hz), 3.94(1H, m), 3.78(1H, m), 3.52(2H, m), 3.16(3H, s).

8) Preparation of the compound represented by the formula

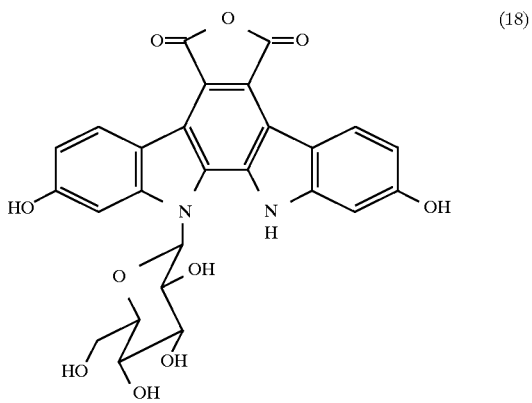

(18)

1.2 g of the compound (17) obtained in Example 6-7) was dissolved in 40 ml of a 10% aqueous solution of potassium hydroxide, and this solution was stirred at room temperature for 1 hour. The reaction mixture was neutralized by the addition of 40 ml of 2N hydrochloric acid, and then extracted with 1 liter of methyl ethyl ketone. The organic layer was washed with a saturated aqueous solution of sodium chloride, dried and concentrated. The resulting residue was recrystallized from acetone-heptane to obtain 1.2 g of the desired compound (18) (in a 100% yield).

HRMS (m/z): found 520.1147, calcd 520.1118 [as $C_{26}H_{20}N_2O_{10}$]

IR (KBr, cm$^{-1}$): 3311, 1810, 1739, 1652, 1626, 1558, 1405, 1091, 611.

$^1$H-NMR (300 MHz, DMSO-d$_6$, δ ppm): 11.4(1H, s), 9.95(1H, S), 9.92(1H, s), 8.69(1H, d, J=7.7 Hz), 8.63(1H, d, J=7.7 Hz), 7.25(1H, d, J=1.5 Hz), 7.03(1H, d, J=1.5 Hz), 6.90(1H, dd, J=1.5, 7.7 Hz), 6.87(1H, d, J=1.5, 7.7 Hz), 6.06(1H, d, J=8.0 Hz), 5.95(1H, t, J=4.6 Hz), 5.38(1H, d, J=5.1 Hz), 5.16(1H, d, J=5.2 Hz), 4.99(1H, d, J=5.2 Hz), 3.30–4.10(6H, m).

9) 500 mg of the compound (18) obtained in Example 6-8) was dissolved in 50 ml of DMF, and 152 mg of 2-hydrazino-1,3-propanediol was added thereto. This mixture was stirred at 80° C. for 1 hour. After the reaction mixture was concentrated, the resulting residue was purified with Sephadex LH-20 (chloroform-methanol-ethanol-water=5:2:2:1) to obtain 418 mg of the title compound [I-B] (in a 77% yield).

HRMS (m/z): found 609.1816, calcd 609.1833 [as $C_{29}H_{28}N_4O_{11}$]

IR (KBr, cm$^{-1}$): 3415, 3353, 1749, 1652, 1575, 1540, 1375, 1197, 609.

$^1$H-NMR (300 MHz, DMSO-d$_6$, δ ppm): 11.20(1H, s), 9.78(1H, s), 9.75(1H, s), 8.87(1H, d, J=8.6 Hz), 8.79(1H, d, J=8.6 Hz), 7.18(1H, d, J=2.0 Hz), 6.98(1H, d, J=2.0 Hz), 6.82(1H, dd, J=2.0, 8.6 Hz), 6.80(1H, dd, J=2.0, 8.6 Hz), 5.97(1H, d, J=8.3 Hz), 5.86(1H, d, J=3.8 Hz), 5.55(1H, d, J=2.6 Hz), 5.32(1H, d, J=4.6 Hz), 5.11(1H, d, J=5.3 Hz), 4.91(1H, d, J=5.1 Hz), 4.53(2H, t, J=5.4 Hz), 4.02(1H, m), 3.85–3.95(2H, m), 3.78(1H, m), 3.40–3.60(6H, m), 3.20–3.30(1H, m).

EXAMPLE 7

Preparation of the compound represented by the formula

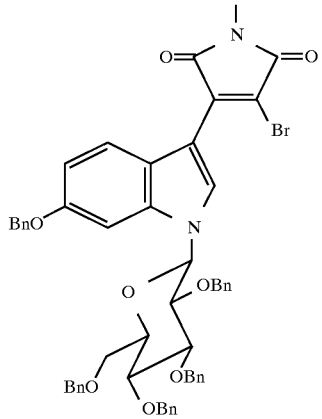

(19)

1.00 g of the compound (11) obtained in Example 6-1), 6.57 g of 2,3,4,6-O-tetrabenzyl-D-glucopyranose and 3.19 g of triphenylphosphine were dissolved in 40 ml of THF, and 1.91 ml of azodicarboxylic acid diethyl ester was added thereto at 0° C. This mixture was stirred for 1 hour, during which time the temperature was gradually raised to room temperature. The reaction mixture was partitioned between 200 ml of ethyl acetate and 100 ml of aqueous ammonium chloride. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=8:1 to 4:1) to obtain 3.07 g of the desired compound (19) (in a 91% yield).

HRMS (m/z): found 932.2694, calcd 932.2627 [as $C_{54}H_{49}N_2O_8Br$]

IR (KBr, cm$^{-1}$): 1767, 1707, 1603, 1454, 1379, 1090, 1026.

$^1$H-NMR (300 MHz, CDCl$_3$, δ ppm): 7.96(1H, d, J=8.9 Hz), 7.93(1H, s), 7.17–7.41(20H, m), 6.97–7.17(5H, m), 6.71(2H, dd, J=1.3, 8.9 Hz), 5.29(1H, d, J=8.4 Hz), 5.00(1H, d, J=7.8 Hz), 4.97(1H, d, J=7.8 Hz), 4.93(1H, d, J=11.9 Hz), 4.92(1H, d, J=10.8 Hz), 4.90(1H, d, J=11.9 Hz), 4.68(1H, d, J=10.8 Hz), 4.61(1H, d, J=11.9 Hz), 4.52(1H, d, J=11.9 Hz), 4.17(1H, d, J=10.0 Hz), 3.75–3.96(5H, m), 3.71(1H, brd, J=9.6 Hz), 3.56(1H, d, J=10.0 Hz), 3.16(3H, s).

EXAMPLE 8

Preparation of the compound represented by the formula

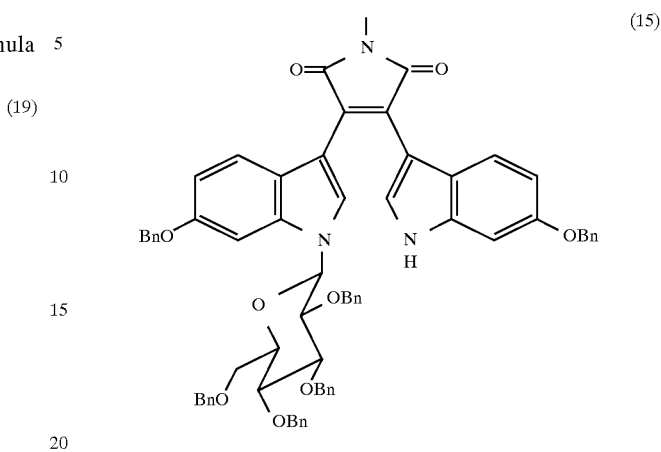

(15)

350.6 mg of 6-benzyloxyindole was dissolved in 5 ml of THF, and 3.45 ml of lithium hexamethyldisilazide (as a 1M solution in THF) was added thereto. After this mixture was stirred under an atmosphere of nitrogen at 0 for 15 minutes, 15 ml of a THF solution containing 1,470 mg of the compound (19) was added dropwise thereto over a period of 10 minutes. After completion of the addition, the resulting mixture was stirred at room temperature for 1 hour. The reaction mixture was poured into 100 mL of 2N hydrochloric acid and extracted with 200 mL of ethyl acetate. The organic layer was washed with water, a saturated aqueous solution of sodium hydrogen carbonate and then a saturated aqueous solution of sodium chloride, dried and concentrated. The resulting residue was purified by silica gel chromatography (hexane-ethyl acetate=4:1 to 1:1) to obtain 1,234 mg of the desired compound (15) (in a 73% yield).

Its property data agreed with those obtained in Example 6-5).

EXAMPLE 9

Preparation of the compound represented by the

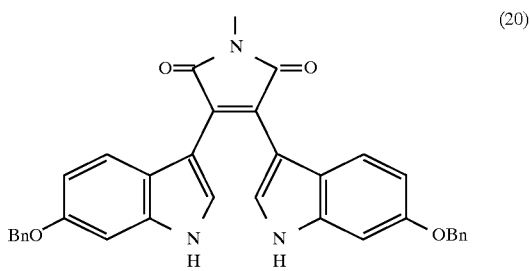

(20)

100 mg of the compound (13) obtained in Example 6-3) was dissolved in 10 ml of methylamine (as a 40% solution in methanol), and this solution was stirred at room temperature for 30 minutes. After the reaction mixture was concentrated, the resulting residue was recrystallized from dichloromethane-acetone-hexane to obtain 68.6 m of the desired compound (20) (in a 84% yield).

HRMS (m/z): found 553.1982, calcd 553.2002 [as $C_{35}H_{27}N_3O_4$]

IR (KBr, cm$^{-1}$) 3419, 3350, 1759, 1697, 1620, 1533, 1454, 1383, 1292, 1167.

$^1$H-NMR (300 MHz, DMSO-$d_6$, δ ppm): 11.48(2H, s), 7.62(2H, s), 7.28–7.45(10H, m), 6.95(2H, d, J=1.2 Hz), 6.70(2H, d, J=8.7 Hz), 6.39(2H, dd, J=1.2, 8.7 Hz), 5.04(4H, s), 3.03(3H, s).

EXAMPLE 10

Preparation of the compound represented by the formula

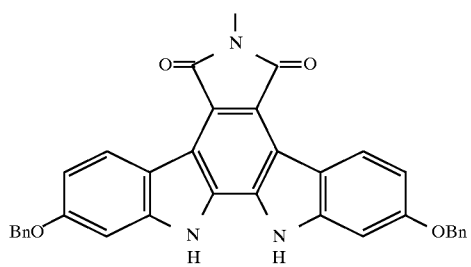
(21)

1.01 9 of the compound (20) obtained in Example 9 and 456.1 mg of 2,3-dichloro-5,6-dicyano-1,4- benzoquinone were dissolved in 50 ml of toluene, and this solution was stirred at 110° C. for 40 minutes. After the reaction mixture was returned to room temperature, the insoluble matter was filtered off and washed with 30 ml of methanol. The residue was recrystallized from dimethyl sulfoxide-dichloromethane-methanol to obtain 981 mg of the desired compound (21) (in a 98% yield).

HRMS (m/z): found 551.1829, calcd 551.1845 [as $C_{35}H_{25}N_3O_4$]

IR (KBr, cm$^{-1}$): 3257, 1740, 1675, 1620, 1571, 1402, 1246, 1178.

$^1$H-NMR (300 MHz, DMSO-$d_6$, δ ppm): 11.46(2H, s), 8.79(2H, d, J=8.5 Hz), 7.53(4H, d, 8.5 Hz), 7.35–7.44(8H, m), 7.02(2H, dd, 8.5, 0.8 Hz), 5.25(4H, s), 3.13(3H, s).

EXAMPLE 11

Preparation of the compound represented by the formula

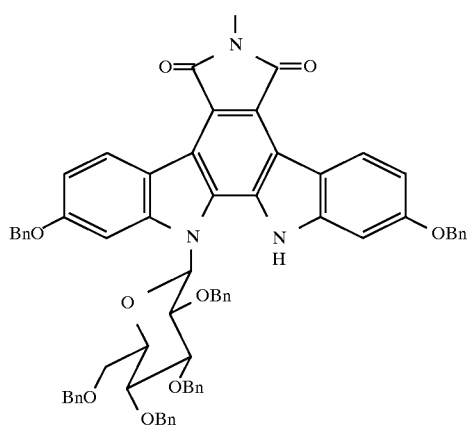
(16)

5.7 g of potassium hydroxide and 22 g of sodium sulfate were suspended in 380 ml of acetonitrile, and 5.51 g of the compound (21) obtained in Example 10 was added thereto. After this mixture was stirred at room temperature for 1 hour, 170 ml of an acetonitrile solution containing 11.5 9 of 1-chloro-2,3,4,6-tetra-O-benzyl-D-glucopyranoside was added dropwise thereto. After the resulting mixture was stirred at room temperature for 7 hours, the reaction mixture was poured into 360 ml of 1N hydrochloric acid and extracted with 360 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (toluene-ethyl acetate=30:1) to obtain 7.8 g of the desired compound (16) (in a 73% yield).

Its property data agreed with those obtained in Example 6-6).

EXAMPLE 12

Preparation of the compound represented by the formula

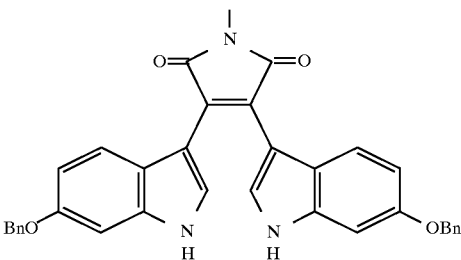
(20)

50 ml of ethylmagnesium bromide (as a 0.9M solution in THF) was dissolved in 50 ml of toluene, and 10 g of 6-benzyloxyindole was added thereto at 45° C. After this mixture was stirred for 1 hour, 50 ml of a toluene solution containing 4.02 g of 2,3-dibromo-N-methylmaleimide was added thereto, followed by stirring at 110° C. overnight. The reaction mixture was poured into 500 ml of 2N hydrochloric acid and extracted with 900 ml of methyl ethyl ketone. The organic layer was washed with water, a saturated aqueous solution of sodium hydrogen carbonate, water and then a saturated aqueous solution of sodium chloride, dried and concentrated. The resulting residue was purified by silica gel chromatography (dichloromethane) and then recrystalized from dichloromethane-acetone-hexane to obtain 5.65 g of the desired compound (20) (in a 69% yield).

Its property data agreed with those obtained in Example 9.

EXAMPLE 13

Preparation of the compound represented by the formula

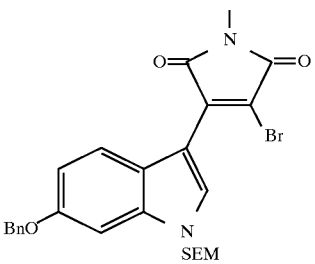
(22)

wherein SEM represents a 2-trimethylsilylethoxymethyl group, and the same will apply hereinafter. 2.00 g of the compound (11) obtained in Example 6-1), 1 g of 2-trimethylsilylethoxymethyl chloride and 300 mg of sodium hydride were dissolved in 30 ml of THF, and this solution was stirred at room temperature for 0.5 hour. The reaction mixture was poured into 200 ml of 2N hydrochloric acid and extracted with 300 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate 4:1) to obtain 1.96 g of the desired compound (22) (in a 77% yield).

¹H-NMR (300 MHz, CDCl₃, δ ppm): 7.96(1H, d, J=8.9 Hz), 7.89(1H, s), 7.33–7.50(5H, m), 7.10(1H, d, J=2.2 Hz), 7.01(1H, dd, J=2.2, 8.9 Hz), 5.48(2H, s), 5.15(2H, s), 3.52(2H, t, J=8.1 Hz), 3.16(3H, s), 0.90(2H, t, J=8.1 Hz), −0.04(9H, s).

EXAMPLE 14

Preparation of the compound represented by the formula

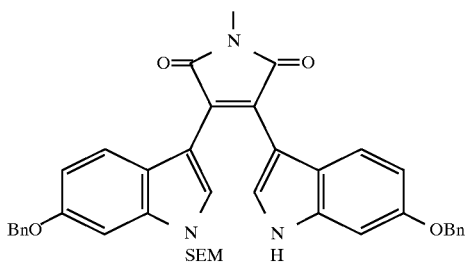

(23)

1.25 g of 6-benzyloxyindole was dissolved in 20 ml of THF, and 2.35 ml of lithium hexamethyldisilazide (as a 1M solution in THF) was added thereto. After this mixture was stirred under an atmosphere of nitrogen at 0° C. for 30 minutes, 20 ml of a THF solution containing 1.96 g of the compound (22) obtained in Example 13 was added dropwise thereto, followed by stirring for 2 hours. The reaction mixture was poured into 100 mL of 2N hydrochloric acid and extracted with 200 mL of ethyl acetate. The organic layer was washed with water, a saturated aqueous solution of sodium hydrogen carbonate and then a saturated aqueous solution of sodium chloride, dried and concentrated. The resulting residue was purified by silica gel chromatography (hexane-ethyl acetate=4:1) and then recrystallized from ethyl acetate-acetone-hexane to obtain 2.21 g of the desired compound (23) (in a 91% yield).

IR (KBr, cm⁻¹): 3369, 1697, 1621, 1533, 1456, 1385, 1246, 1164, 1091, 1025, 837, 737, 696.

¹H-NMR (300 MHz, CDCl₃, δ ppm): 8.55(1H, d, J=2.0 Hz), 7.67(1H, s), 7.57(1H, d, J=2.0 Hz), 7.27–7.46(10H, m), 7.00(1H, d, J=2.0 Hz), 6.89(1H, d, J=8.9 Hz), 6.80(2H, d, J=8.9 Hz), 6.49(2H, dd, J=2.0, 8.9 Hz), 5.41(2H, s), 5.01 (2H, s), 4.96(2H, s), 3.50(2H, t, J=8.9 Hz), 3.17(3H, s), 0.90(2H, t, J=8.9 Hz), −0.02(9H, s).

EXAMPLE 15

Preparation of the compound represented by the formula

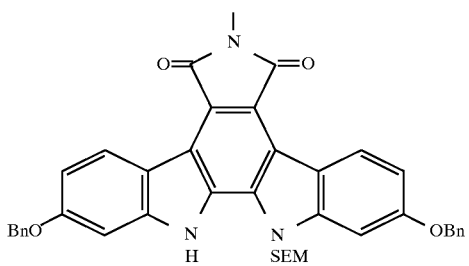

(24)

1.0 g of the compound (23) obtained in Example 14 and 2.0 g of calcium carbonate were dissolved in 50 ml of DMF, and 1.09 g of palladium chloride was added thereto. This mixture was stirred at 80° C. for 0.5 hour. After the reaction mixture was filtered through celite, the filtrate was partitioned between 200 ml of ethyl acetate and 100 ml of 2N hydrochloric acid. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=6:1 to 3:1) and then recrystallized from acetone-hexane to obtain 689 mg of the desired compound (24) (in a 69% yield).

IR (KBr, cm⁻¹): 1747, 1697, 1621, 1581, 1454, 1429, 1376, 1338, 1282, 1251, 1214, 1187, 1132, 1066.

¹H-NMR (300 MHz, CDCl₃, δ ppm): 9.66(1H, brs), 9.00(2H, t, J=8.7 Hz), 7.35–7.53(10H, m), 7.08(2H, dd, J=2.2, 8.7 Hz), 7.06(1H, d, J=2.2 Hz), 7.03(1H, d, J=2.2 Hz), 5.72(2H, s), 5.22(2H, s), 5.21(2H, s), 3.70(2H, t, J=8.1 Hz), 3.09(3H, s), 0.96(2H, t, J=8.1 Hz), −0.05(9H, s).

EXAMPLE 16

Preparation of the compound represented by the formula

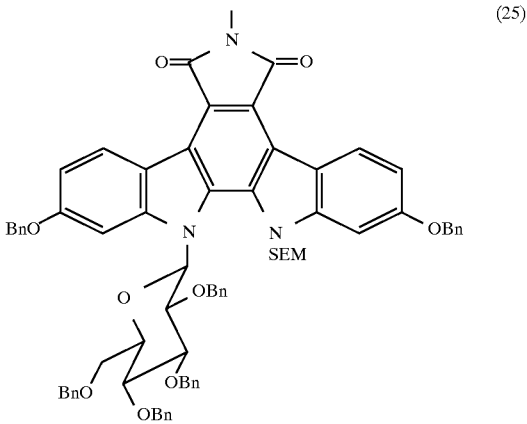

(25)

30 mg of potassium tert-butoxide and 200 mg of sodium sulfate were suspended in 2 ml of toluene, and 50 mg of the compound (24) obtained in Example 15 was added thereto. After this mixture was stirred at room temperature for 0.5 hour, 1 ml of a toluene solution containing 130 mg of 1-chloro-2,3,4,6-tetra-O-benzyl-D-glucopyranoside was added dropwise thereto. After the resulting mixture was stirred at 50° C. overnight, the reaction mixture was poured into 50 ml of 1N hydrochloric acid and extracted with 100 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=8:1 to 6:1) to obtain 58.6 mg of the desired compound (25) (in a 65% yield).

¹H-NMR (300 MHz, CDCl₃, δ ppm): 9.03(1H, d, J=9.5 Hz), 8.99(1H, d, J=9.5 Hz), 6.77–7.57(32H, m), 6.07(2H, d, J=7.5 Hz), 5.30(1H, d, J=8.9 Hz), 5.26(2H, s), 5.13(2H, S), 3.47–5.02(15H, m), 3.42(2H, t, J=8.9 Hz), 3.12(3H, s), 2.61(1H, d, J=9.5 Hz), 0.93(2H, t, J=8.9 Hz), −0.07(9H, s).

EXAMPLE 17

Preparation of the compound represented by the formula

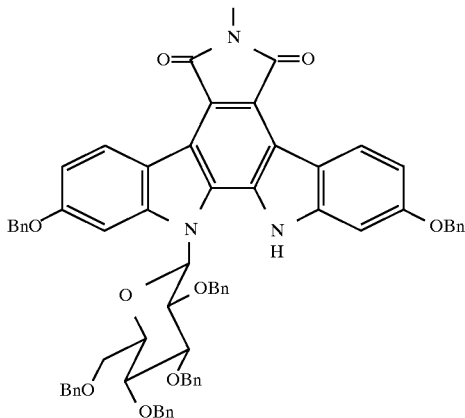
(16)

45 mg of the compound (25) obtained in Example 16, 50 mg of molecular sieve and 0.9 ml of tetra-butylammonium fluoride (as a 1M solution in THF) were dissolved in 1 ml of tetrahydrofuran, and this mixture was stirred at 50° C. for 2 hours. After the reaction mixture was filtered through celite, the filtrate was poured into 50 ml of 1N hydrochloric acid and extracted with 100 ml of ethyl acetate. The organic layer was washed with water, a saturated aqueous solution of sodium hydrogen carbonate, water and then a saturated aqueous solution of sodium chloride, dried and concentrated. The resulting residue was purified by silica gel chromatography (hexane-ethyl acetate=10:1) to obtain 26.7 mg of the desired compound (16) (in a 85% yield).

Its property data agreed with those obtained in Example 6-6).

EXAMPLE 18

Preparation of the compound represented by the formula $$H_2NNHCH(CH_2OH)_2 \quad (26)$$

1) 10.0 g of dihydroxyacetone dimer and 14.7 g of tert-butyl carbazinate were dissolved in 500 ml of ethanol, and this solution was stirred at room temperature for 15 hours. After the reaction mixture was concentrated under reduced pressure, the resulting residue was recrystallized from ethyl acetate to obtain 18.67 9 of 2-(tert-butyloxycarbonyl)-hydrazono-1,3-propanediol as a colorless solid.

$^1$H-NMR (300 MHz, DMSO-d$_6$, δ ppm): 1.49(9H, s), 3.92(2H, d,J=5.2 Hz), 4.24(2H, d, J=5.0 Hz), 4.88(1H, t, J=5.8 Hz), 5.61(1H, t, J=5.1 Hz), 9.98(1H, brs).

2) 50 ml of a borane-tetrahydrofuran complex was added to 5.00 g of 2-(tert-butyloxycarbonyl)-hydrazono-1,3-propanediol at 0° C., and this mixture was stirred at room temperature for 0.5 hour. 25 ml of 6N hydrochloric acid was added to the reaction mixture, and the resulting mixture was heated under reflux for 1.5 hours. After the reaction mixture was concentrated under reduced pressure, the resulting residue was adsorbed to Dowex 50W×4 of the H$^+$ type, washed with water, and eluted with 0.5N aqueous ammonia. After fractions containing the desired product were collected and concentrated under reduced pressure, the resulting oily material was adsorbed to IRC-50 of the NH$_4^+$ type and eluted with water. Fractions containing the desired product were collected and concentrated under reduced pressure to obtain 2.26 g of 2-hydrazino-1,3-propanediol as a colorless solid.

FAB-MS (m/z): 107 (M+H)$^+$ $^1$H-NMR (200 MHz, CD$_3$OD, δ ppm): 2.78(1H, m), 3.50–3.75(4H, m).

REFERENCE EXAMPLE 1

Preparation of the compound represented by the formula

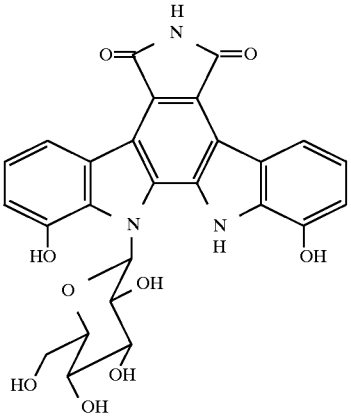
(27)

Microtetraspora sp. A34549 strain [Accession Number: FERM BP-4206 (a microorganism transferred from No. P-13292 deposited with the Research Institute of Microbiological Technology on Nov. 17, 1992) which had been grown on a slant agar medium was inoculated in a 500 ml conical culture flask containing 110 ml of a culture medium (pH 7.2 before sterilization) composed of 0.2% glucose, 2.0% dextrin, 0.5% oatmeal, 0.5% degreased rice bran, 0.2% degreased meat-bone meal, 0.1% dry yeast, 0.05% magnesium sulfate heptahydrate, 0.05% sodium bromide, 0.5% sodium chloride and 0.1% dipotassium hydrogen phosphate, and incubated at 28° C. on a rotary shaker (180 revolutions per minute) for 8 days. 2 ml each of the resulting culture was inoculated in twenty 500 ml conical culture flasks containing 110 ml of a culture medium having the aforesaid composition, and incubated at 28° C. on a rotary shaker (180 revolutions per minute). After 9 days' incubation, 0.5 ml of a 20 mg/ml solution of 12,13-dihydro-1,11-dihydroxy-5H-indolo[2,3-a]pyrrolo[3,4-c]carbazole-5,7(6H)-dione [compound (28); see Japanese Laid-Open Patent No. 2077/'91] in dimethyl sulfoxide was added to each flask, and the incubation was continued under the aforesaid conditions for an additional 15 days.

The culture thus obtained was extracted with 3 liters of methyl ethyl ketone (MEK). After the MEK extract was concentrated under reduced pressure, the resulting concentrate was extracted with ethyl acetate.

The ethyl acetate extract (850 ml) was dehydrated with anhydrous sodium sulfate and then concentrated to dryness. This was subjected to silica gel column chromatography (1.5 cm in inner diameter and 30 cm in length; BW-350 silica gel; manufactured by Fuji-Davison Chemical Co., Ltd.), washed with chloroform-methanol-tetra-hydrofuran-28% aqueous ammonia (2:1:3:0.2), and eluted with chloroform-methanol-tetrahydrofuran (3:1:1). Fractions containing the desired product were collected and concentrated to dryness. The resulting residue was dissolved in a small amount of tetrahydrofuran-ethanol (1:3), subjected to Sephadex LH-20 column chromatography (1.5 cm in inner diameter and 87 cm in length), and eluted with ethanol. Fractions containing the desired product were collected and concentrated to dryness to obtain 53.9 mg of the title compound (27), i.e., 12,13-dihydro-1,11-dihydroxy-13-β-D-glucopyranosyl)-5H-indolo[2,3-a]pyrrolo[3,4-c]-carbazole-5,7(6H)-dione.

HR FAB-MS (m/z): 519.1313

$^1$H-NMR (400 MHz, DMSO-$d_6$, δ ppm): 11.0(1H, s), 10.9(1H, s), 10.3(1H, brs), 9.93(1H, brs), 8.69(1H, d, J=7.8 Hz), 8.51(1H, d, J=7.8 Hz), 7.17(2H, t, J=7.8 Hz), 7.05(1H, d, J=9.3 Hz), 7.01(1H, d, J=7.8 Hz), 6.99(1H, d, J=7.8 Hz), 5.41(1H, d, J=5.9 Hz), 5.34(1H, brs), 5.20(1H, d, J=5.4 Hz), 4.89(1H, brs), 4.02(2H, m), 3.74(1H, m), 3.63(2H, m), 3.41(1H, m).

REFERENCE EXAMPLE 2

Preparation of the compound represented by the formula

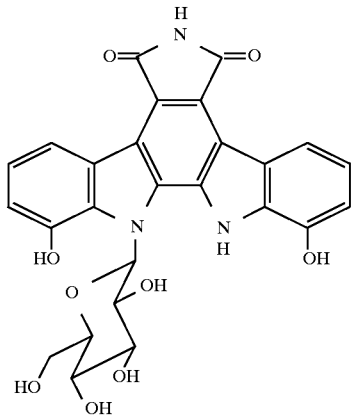

(27)

Saccharothrix aerocolonigenes ATCC 39243 strain which had been grown on a slant agar medium was inoculated in seven 500 ml conical culture flasks containing 110 ml of a culture medium (pH 7.2 before sterilization) composed of 3.0% glucose, 1.0% soya flour, 1.0% cottonseed cake and 0.3% calcium carbonate, and incubated at 28° on a rotary shaker (180 revolutions per minute) for 48 hours. 4 ml each of the resulting culture was inoculated in one hundred and fifty 500 ml conical culture flasks containing 110 ml of a culture medium (pH 7.2 before sterilization) composed of 1.0% glucose, 6.0% dextrin, 1.5% linseed cake, 0.5% powdered yeast, 0.1% ferrous sulfate heptahydrate, 0.1% ammonium dihydrogen phosphate, 0.1% ammonium sulfate and 1.0% calcium carbonate, and incubated at 28° C. on a rotary shaker (180 revolutions per minute). After 120 hours' incubation, 0.5 ml of a 20 mg/ml solution of 12,13-dihydro-1,11-dihydroxy-5H-indolo[2,3-a]pyrrolo[3,4-c]-carbazole-5,7(6H)-dione [see Japanese Laid-Open Patent No. 2077/'91] in dimethyl sulfoxide (DMSO) was added to each flask, and the incubation was continued under the aforesaid conditions for an additional 120 hours.

The microbial cells separated by filtering the culture thus obtained was extracted twice with methanol (5.1 liters and 5.6 liters) and twice with tetrahydrofuran (2.2 liters and 2.3 liters). The methanol and tetrahydrofuran extracts were combined and concentrated to about 1,600 ml. The aqueous solution obtained by concentration was extracted with hexane (780 ml) to remove any impurities, and the aqueous layer was extracted with 3.3 liters of ethyl acetate. After the ethyl acetate extract was concentrated to dryness, the resulting residue was washed with about 90 ml of ethyl acetate and then extracted with about 90 ml of methanol. The methanol extract was concentrated to dryness to obtain 694 mg of a yellow-orange solid. This was dissolved in 40 ml of methanol and subjected to Sephadex LH-20 column chromatography (3.0×53 cm; manufactured by Pharmacia Co.) using methanol as the eluent. Fractions containing the desired compound were collected and concentrated to dryness. The resulting residue was subjected to silica gel column chromatography (1.5×46 cm; Kieselgel 60; manufactured by Merck Co.), washed with chloroform and then with chloroform-methanol (10:1), and eluted with ethyl acetate-methanol (10:1). The eluate was concentrated to dryness to obtain 169 mg of the desired title compound (27), i.e., 12,13-dihydro-1,11-dihydroxy-13-(β-D-glucopyranosyl)-5H-indolo[2,3-a]pyrrolo[3,4-c]carbazole-5,7(6H)-dione.

The property data of the title compound thus obtained were identical to those of the compound obtained in Reference Example 1.

REFERENCE EXAMPLE 3

Preparation of the compound represented by the formula

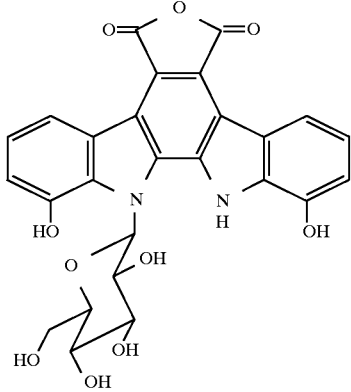

(8)

3.4 g of the 12,13-dihydro-1,11-dihydroxy-13-(β-D-glucopyranosyl)-5H-indolo[2,3-a]pyrrolo[3,4-c]-carbazole-5,7(6H)-dione prepared in Reference Example 1 or 2 was dissolved in 120 ml of a 10% aqueous solution of potassium hydroxide, and this solution was stirred at room temperature for 2 hours. After the reaction mixture was neutralized by the addition of 120 ml of 2N hydrochloric acid, the precipitated red crystals were separated by filtration, washed with water and dried to obtain 3.0 g of the title compound (8).

FAB-MS (m/z): 520 (M)$^+$, 521 (M+H)$^+$ $^1$H-NMR (400 MHz, DMSO-$d_6$, δ ppm): 3.42(1H, m), 3.56–3.70(2H, m), 3.76(1H, m), 3.95–4.10(2H, m), 4.95(1H, d, J=4.6 Hz), 5.24(1H, d, J=5.4 Hz), 5.32(1H, dd, J=4.9, 5.1 Hz), 7.06(2H, dd, J=7.6, 7.8 Hz), 7.09(1H, d, J=8.0 Hz), 7.20(1H, d, J=7.8 Hz), 7.40(1H, d, J=7.8 Hz), 8.36(1H, d, J=7.6 Hz), 8.51(1H, d, J=7.6 Hz), 10.13(1H, s), 10.52(1H, s), 11 .11(1 H, s).

Exploitability in Industry

The compounds of the present invention have an excellent antitumor effect and are hence useful as antitumor agents in the field of medicine.

We claim:

1. A process for the preparation of a compound of formula [I]

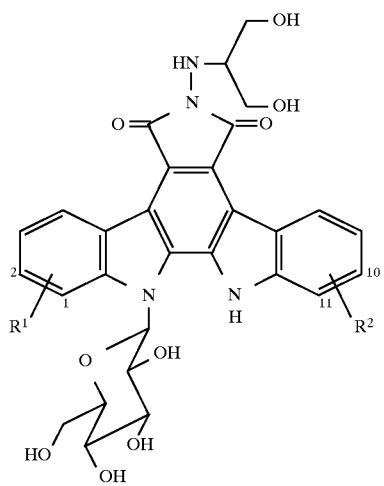

wherein $R^1$ and $R^2$ each represent an OH group, $R^1$ is located at the 1- or 2-position, $R^2$ is located at the 10- or 11-position, $R^2$ is located at the 11-position when $R^1$ is located at the 1-position, and $R^2$ is located at the 10-position when $R^1$ is located at the 2-position which comprises reacting a compound of formula [IX]

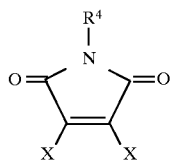

wherein $R^4$ represents a hydrogen atom, a lower alkyl group, a benzyloxymethyl group or an aralkyl group, and X represents a leaving group;

with a compound of formula [X]

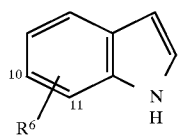

wherein $R^6$ represents a protected OH group located at the 10- or 11-position, in the presence of an organometallic compound to form a compound of formula [XI]

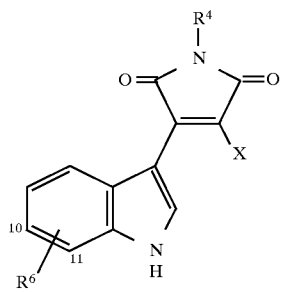

wherein $R^4$, $R^6$ and X and defined above;

protecting the hydrogen atom of the amino group of the indole skeleton to form a compound of formula [XII]

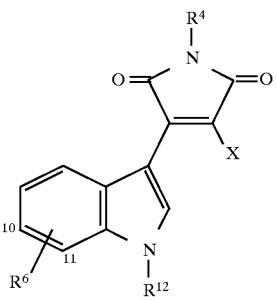

wherein $R^4$, $R^6$ and X are defined above, and $R^{12}$ represents a protecting group for the amino group of the indole skeleton;

reacting the compound of formula [XII] with a compound of formula [XIII]

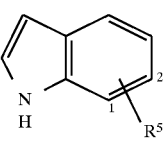

wherein $R^5$ represents a protected OH group at the 1- or 2-position, in the presence of an organometallic compound, to form a compound of formula [XIV]

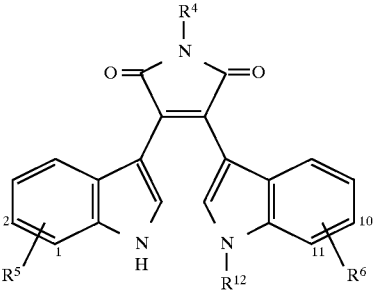

wherein $R^4$, $R^5$, $R^6$, and $R^{12}$ are defined above and $R^5$ and $R^6$ are located at the 1- and 11-positions, respectively or are located at the 2- and 10-positions, respectively;

reacting the compound of formula [XIV] with a compound of formula [XV]

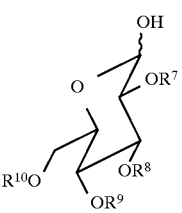

wherein $R^7$, $R^8$, $R^9$, and $R^{10}$, may be the same or different and each represents a protecting group for a hydroxyl group, by the Mitsunobu reaction, to form a compound of formula [XVI]

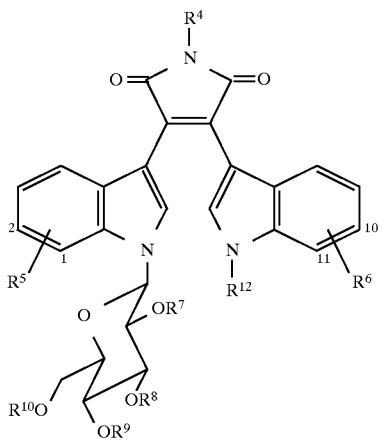

wherein $R^4$ to $R^{10}$ and $R^{12}$ and defined above;

removing the protecting group for the amino group of the indole skeleton to form a compound of formula [XVII]

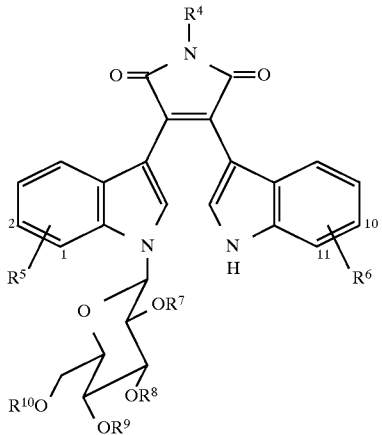

wherein $R^4$ to $R^{10}$ are defined above;

cyclizing the compound of formula [XVII] with the aid of an oxidizing agent to form a compound of formula [XVIII]

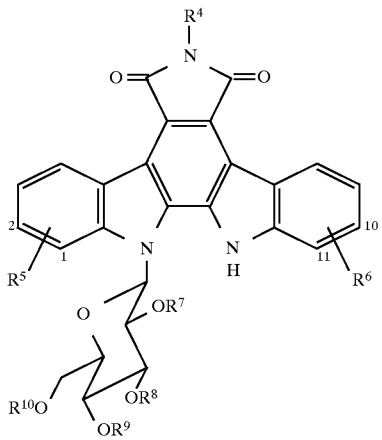

wherein $R^4$ to $R^{10}$ are defined above;

removing the protecting groups for OH groups to form a compound of formula [XIX]

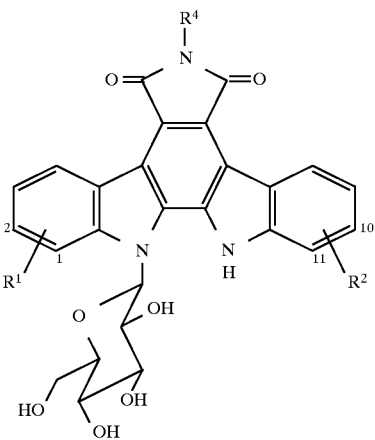

wherein $R^1$ and $R^2$ each represent an OH group, and $R^1$ and $R^2$ are located at the 1- and 11-positions, respectively, or $R^1$ and $R^2$ are located at the 2- and 10-positions, respectively, and $R^4$ is defined above;

reacting the compound of formula [XIX] with a base to form a compound of formula [XX]

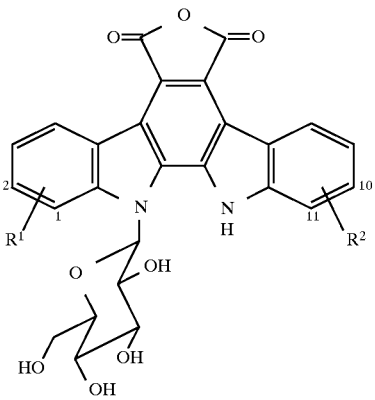

wherein $R^1$ and $R^2$ are defined above; and reacting the compound of formula [XX] with $H_2NNHCH(CH_2OH)_2$ to form a compound of formula [I].

2. A process for the preparation of a compound of general formula [XVIII]

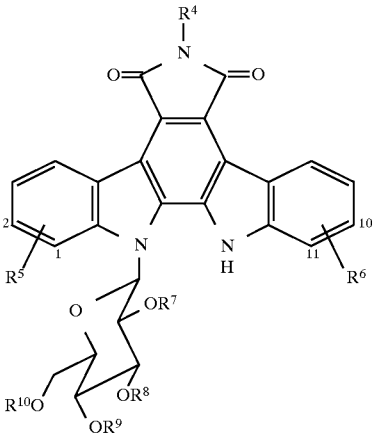

wherein $R^4$ represents a hydrogen atom, a lower alkyl group, a benzyloxymethyl group or an aralkyl group, and X represents a leaving group;

$R^5$ represents a protected OH group at the 1- or 2-position, $R^6$ represents a protected OH group located at the 10- or 11-position, and $R^7$, $R^8$, $R^9$, and $R^{10}$, may be the same or different and each represents a protecting group for a hydroxyl group, which comprises, removing the protective group for the amino group of an indole skeleton from a compound of general formula [XIV]

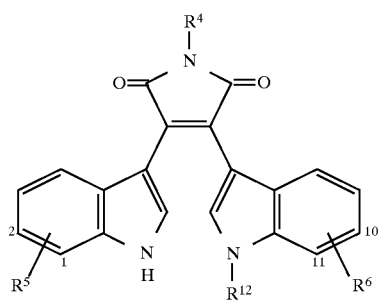
[XIV]

wherein $R^4$ to $R^6$ are defined above, and $R^{12}$ represents a protecting group for the amino group of the indole skeleton, to form a compound of general formula [XXII]

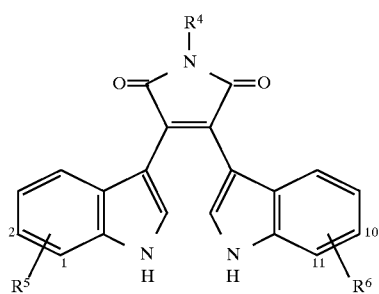
[XXII]

wherein $R^4$ to $R^6$ are defined above;

cyclizing the compound of formula [XXII] with an oxidizing agent, to form a compound of general formula [XXIV]

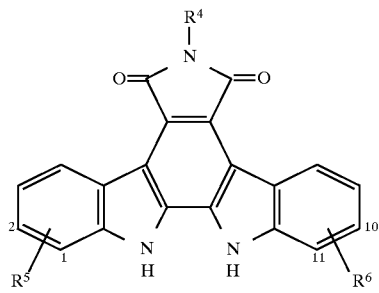
[XXIV]

wherein $R^4$ to $R^6$ are defined above; and reacting the compound of formula [XXIV] with a compound of general formula [XXIII]

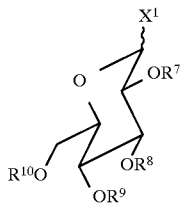
[XXIII]

wherein $R^7$ to $R^{10}$ are defined above, and $X^1$ represents a leaving group, in the presence of a base.

3. A process for the preparation of a compound of general formula [XVIII]

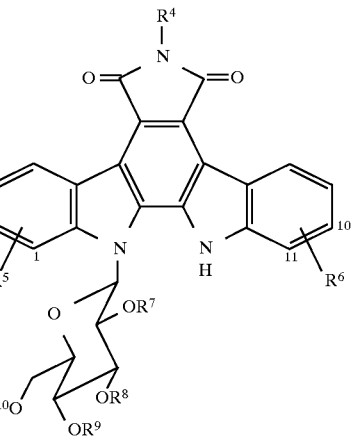
[XVIII]

wherein $R^4$ represents a hydrogen atom, a lower alkyl group, a benzyloxymethyl group or an aralkyl group;

$R^5$ represents a protected OH group at the 1- or 2-position, $R^6$ represents a protected OH group located at the 10- or 11-position, and $R^7$, $R^8$, $R^9$, and $R^{10}$, may be the same or different and each represents a protecting group for a hydroxyl group, which comprises, preparing a compound of general formula [XIV]

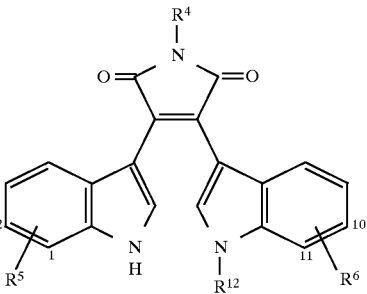
[XIV]

wherein $R^4$ to $R^6$ are defined above, and $R^{12}$ represents a protecting group for the amino group of the indole skeleton;

reacting the compound of formula [XIV] with an oxidizing agent, to form a compound of general formula [XXV]

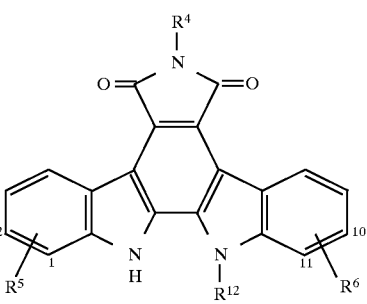
[XXV]

wherein $R^4$ to $R^6$ and $R^{12}$ are defined above;

reacting the compound of formula [XXV] with a compound of general formula [XXIII]

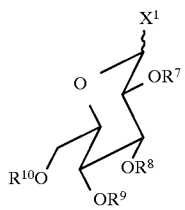

wherein $R^7$ to $R^{10}$ are defined above, and $X^1$ represents a leaving group, in the presence of a base to form a compound of general formula [XXVI]

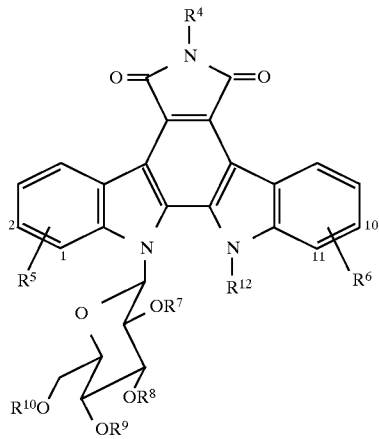

wherein $R^4$ to $R^{10}$ and $R^{12}$ are defined above; and
removing the protecting group for the amino group of the indole skeleton.

4. A process for the preparation of a compound of formula [XVIII]

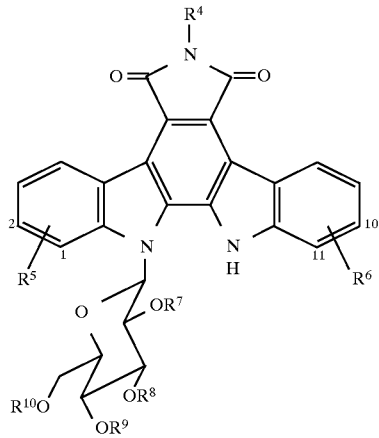

wherein $R^4$ represents a hydrogen atom, a lower alkyl group, a benzyloxymethyl group or an aralkyl group;

$R^5$ represents a protected OH group at the 1- or 2-position,
$R^6$ represents a protected OH group located at the 10- or 11-position, and $R^5$ is located at position-1 when $R^6$ is at position-11 and $R^5$ is located at position-2 when $R^6$ is at position-10; and $R^7$, $R^8$, $R^9$, and $R^{10}$, may be the same or different, and each represents a protecting group for a hydroxyl group;

which comprises reacting a compound of formula [XXV]

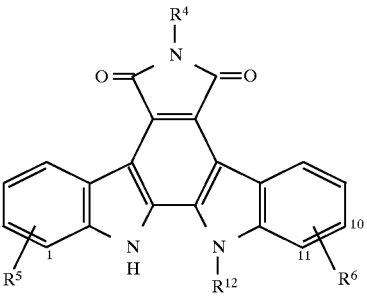

wherein $R^4$ to $R^6$ and $R^{12}$ are defined above and $R^{12}$ represents a protecting group for the amino group of the indole skeleton, with a compound of formula [XXIII]

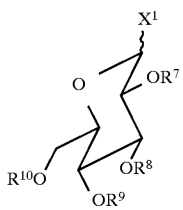

wherein $R^7$ to $R^{10}$ are defined above and $X^1$ represents a leaving group; in the presence of a base to form a compound of formula [XXVI]

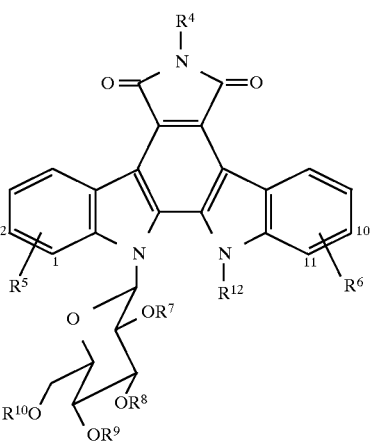

wherein $R^4$ to $R^{10}$ and $R^{12}$ are defined above, and removing the protecting group for the amino group of the indole skeleton.

5. The process of any one of claims 2, 3, or 4 wherein base is KOH, tert-BuOK, NaH, $K_2CO_3$ or lithium hexamethyldisilazide.

6. A composition comprising a compound of formula [I] having antitumor activity,

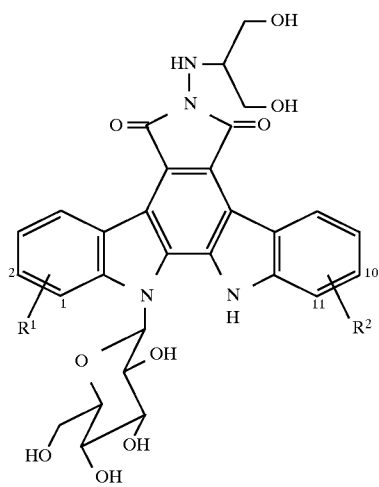

[I]

wherein $R^1$ and $R^2$ each represent an OH group, $R^1$ is located at the 1- or 2-position, $R^2$ is located at the 10- or 11-position, $R^2$ is located at the 11-position when $R^1$ is located at the 1-position, and $R^2$ is located at the 10-position when $R^1$ is located at the 2-position and a pharmaceutically acceptable carrier.

7. A composition as set forth in claim 6 wherein in the compound of formula [I] $R^1$ and $R^2$ are located at position-1 and position-11, respectively.

8. A composition as set forth in claim 6 wherein in the compound of formula [I] $R^1$ and $R^2$ are located at position-2 and position-10, respectively.

* * * * *